US011965866B2

(12) United States Patent
Micalizzi et al.

(10) Patent No.: US 11,965,866 B2
(45) Date of Patent: Apr. 23, 2024

(54) CALIBRATION OF GAS SENSORS

(71) Applicant: CLARITY MOVEMENT CO., Oakland, CA (US)

(72) Inventors: Paolo Micalizzi, San Francisco, CA (US); Baljot Singh, Daly City, CA (US); Deepak Talwar, San Jose, CA (US); Dengjun Lu, El Cerrito, CA (US)

(73) Assignee: Clarity Movement Co., Berkeley, CA (US)

( * ) Notice: Subject to any disclaimer, the term of this patent is extended or adjusted under 35 U.S.C. 154(b) by 38 days.

(21) Appl. No.: 17/350,902

(22) Filed: Jun. 17, 2021

(65) Prior Publication Data

US 2021/0311004 A1  Oct. 7, 2021

Related U.S. Application Data

(62) Division of application No. 15/929,156, filed on Oct. 31, 2019, now Pat. No. 11,300,549.

(60) Provisional application No. 62/753,548, filed on Oct. 31, 2018.

(51) Int. Cl.
| G01N 33/00 | (2006.01) |
| G01D 11/24 | (2006.01) |
| H04Q 9/02  | (2006.01) |
| H04W 4/38  | (2018.01) |

(52) U.S. Cl.
CPC ..... *G01N 33/0006* (2013.01); *G01N 33/0075* (2013.01); *H04Q 9/02* (2013.01); *G01D 11/245* (2013.01); *H04Q 2209/40* (2013.01); *H04Q 2209/886* (2013.01); *H04W 4/38* (2018.02)

(58) Field of Classification Search
CPC .............. G01N 33/0006; G01N 33/0075
See application file for complete search history.

(56) References Cited

U.S. PATENT DOCUMENTS

| 5,801,297 A  | 9/1998 | Mifsud et al. |
| 6,606,897 B1 | 8/2003 | Koyano et al. |
| 8,503,943 B2 | 8/2013 | Spanhake |

(Continued)

FOREIGN PATENT DOCUMENTS

WO  2017/054098 A1  4/2017

OTHER PUBLICATIONS

Aeroqual AQY 1 Specification Sheet MRK-D-504 v2, Aeroquai Ltd., 2 pages.

(Continued)

*Primary Examiner* — Natalie Huls
(74) *Attorney, Agent, or Firm* — Van Court & Aldridge LLP

(57) ABSTRACT

A sensor node includes a sensor node printed circuit board, a sensor module, and a communication module. The sensor node printed circuit board manages power of the sensor node circuitry, the sensor module and the communication module such that power is provided from a primary power supply supplemented by a secondary power supply. The sensor module includes a plurality of air quality sensors to measure the concentration of air pollutants. The sensor module may be replaceable. The communication module may communicate air quality measurements to and receive configurations from a data management platform, which may perform processes to improve the accuracy of the air quality measurements.

30 Claims, 13 Drawing Sheets

(56) References Cited

U.S. PATENT DOCUMENTS

| | | | |
|---|---|---|---|
| 9,010,316 B1 | 4/2015 | Corbell, Sr. | |
| 9,291,608 B2* | 3/2016 | Herzl | G01N 33/0006 |
| 9,311,807 B2* | 4/2016 | Schultz | G06F 13/4221 |
| 10,145,827 B2 | 12/2018 | Risk et al. | |
| 10,488,064 B1 | 11/2019 | Crowder et al. | |
| 2004/0069046 A1* | 4/2004 | Sunshine | G01N 33/0009 422/90 |
| 2004/0139110 A1* | 7/2004 | LaMarca | H04L 67/02 |
| 2006/0077611 A1 | 4/2006 | Bender et al. | |
| 2008/0028827 A1 | 2/2008 | Andrews et al. | |
| 2008/0040041 A1 | 2/2008 | Kilgus | |
| 2011/0248846 A1 | 10/2011 | Belov et al. | |
| 2011/0276738 A1 | 11/2011 | Kim et al. | |
| 2012/0079871 A1 | 4/2012 | Williamson | |
| 2013/0007316 A1 | 1/2013 | Moon et al. | |
| 2016/0077071 A1 | 3/2016 | Chancey | |
| 2016/0370338 A1 | 12/2016 | Sayfan | |
| 2017/0003154 A1 | 1/2017 | Mais et al. | |
| 2017/0023458 A1 | 1/2017 | Hart et al. | |
| 2017/0102251 A1 | 4/2017 | Masson | |
| 2017/0184560 A1 | 6/2017 | Crescini et al. | |
| 2017/0208493 A1* | 7/2017 | Masson | H04W 4/38 |
| 2018/0120279 A1 | 5/2018 | Yi et al. | |
| 2018/0156766 A1* | 6/2018 | Zeng | G01N 33/004 |
| 2019/0011416 A1 | 1/2019 | Worth | |
| 2019/0033278 A1* | 1/2019 | Mou | G08B 21/12 |
| 2019/0217681 A1 | 7/2019 | Lin et al. | |
| 2019/0373426 A1* | 12/2019 | Combs | H04W 4/00 |
| 2020/0093088 A1 | 3/2020 | Carta | |
| 2020/0400597 A1 | 12/2020 | Barbul et al. | |
| 2021/0018210 A1 | 1/2021 | Nasis | |
| 2022/0099640 A1* | 3/2022 | Lebegue | G01N 33/0075 |

OTHER PUBLICATIONS

Sensor List, Air Quality Sensor Performance Evaluation Center (AQ-SPEC), South Coast Air Quality Management District, Aug. 22, 2019, 14 pages.

\* cited by examiner

CALIBRATION OF GAS SENSORS

CROSS-REFERENCE TO RELATED APPLICATIONS

This application is a divisional of U.S. patent application Ser. No. 15/929,156, filed Oct. 31, 2019, which claims priority to U.S. Provisional Patent Application No. 62/753,548, entitled "ATMOSPHERIC MONITORING SENSOR NODE", filed Oct. 31, 2018, in the United States Patent Office, each of which is incorporated by reference.

BACKGROUND

Air pollution is a leading cause of premature deaths worldwide and represents a high cost in terms of welfare spending. Therefore, governments and other organizations are mandated to monitor air quality and reduce exposure of people to air pollution. Conventionally, air quality within a given region, for example in a city, is monitored using expensive monitoring equipment with bulky size, high cost, and high maintenance requirements. Due to budget and space constraints, the conventional monitoring systems and methods may only be deployed at sparse locations within the region, which limits the ability of acquiring air quality information with high spatiotemporal resolution. The limitations in air quality information may hinder the ability to take effective actions for reducing air pollution. To address the need for air quality information with higher spatiotemporal resolution, the deployment of dense networks composed of numerous low-cost, internet connected environmental sensors (sensor nodes) is attractive. However, the accuracy of sensor nodes may be lower than that of the conventional monitoring equipment (monitors), which causes concerns regarding the accuracy of the information they acquire. Therefore, there is a need to provide systems and methods for hyperlocal monitoring of air quality within a given region with high spatiotemporal resolution and high measurement accuracy. Furthermore, increasing the number of monitoring sites could result in an increase of device deployment and maintenance cost. Thus, there is a need for systems that can be efficiently deployed and maintained.

BRIEF SUMMARY

One or more improved systems, methods, and/or apparatuses acquire air quality measurements within a given region with high spatiotemporal resolution and high measurement accuracy. Hyperlocal monitoring of air quality within a given region may occur through the deployment of a dense network of environmental sensor nodes. Systems, methods, and/or apparatuses are further provided to ensure and enhance the accuracy of the measurements of said sensor nodes, and that enable the quick and scalable deployment of a dense network of said sensor nodes.

A compact sensor apparatus is disclosed, which comprises a power module configured to supply a reliable power supply from a primary power source supplemented by a secondary power source. The apparatus further comprises a sensor module configured to monitor a gas, such as ambient air, for one or more characteristics. The apparatus comprises a communication module configured to establish a wireless communication channel over a network with a host. The apparatus further comprises a controller configured to manage the sensor module and to send measurement data to the host by way of the wireless communication channel. The apparatus comprises a printed circuit board configured to interconnect the power module, reliable power supply, controller, and communication module. Finally, the apparatus comprises an enclosure configured to house the printed circuit board, power module, sensor module, communication module, and controller.

A system is disclosed comprising an interchangeable sensor module configured to monitor an air sample for one or more characteristics. The system further comprises an enclosure comprising the interchangeable sensor module, a power module configured to supply power, a communication module configured to establish a wireless communication channel over a network with a host, a controller configured to manage the interchangeable sensor module and to send measurement data to the host by way of the wireless communication channel. Finally, the system comprises a universal mount configured to mount the enclosure in a plurality of mounting configurations.

A method is disclosed, which comprises placing a first sensor node near a reference monitor within a region. The method next comprises placing a plurality of sensor nodes at various locations within the region. The method further comprises gathering measurement data from the first sensor node, the reference monitor, and the plurality of sensor nodes. Then the method comprises determining a calibration profile for each of the first sensor node and the plurality of sensor nodes based on measurement data from the reference monitor. Finally, the method comprises applying the calibration profile for each of the first sensor node and the plurality of sensor nodes to measurement data from each of the first sensor node and the plurality of sensor nodes to obtain calibrated measurement data for each of the sensor nodes.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
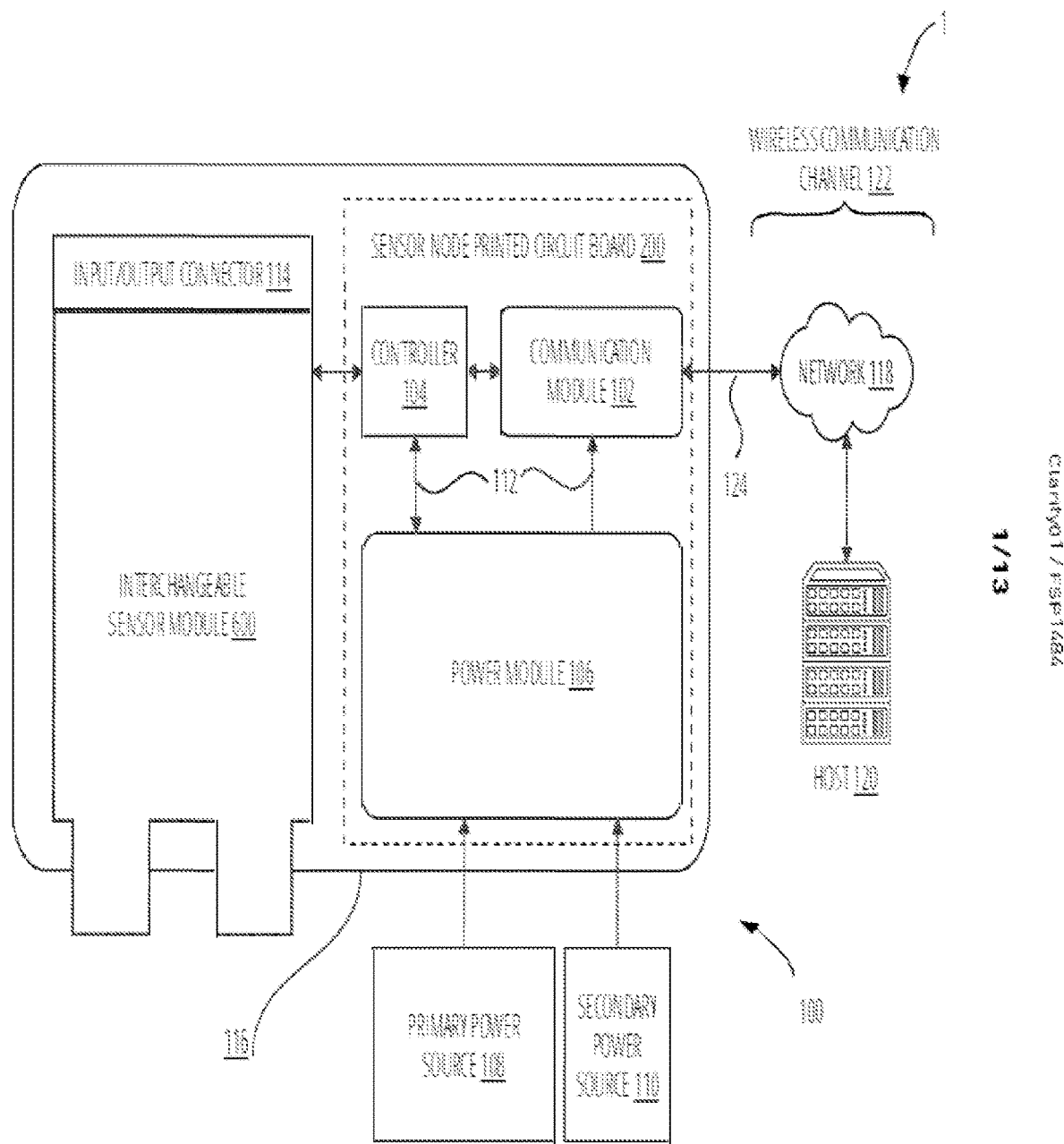
FIG. 1 illustrates a schematic view of an embodiment of a sensor node 100.

A compact sensor apparatus in the form of a sensor node is disclosed herein. The sensor node may be considered compact in that it may be between 50 mm and 200 mm in length, between 40 mm and 100 mm in width, and between 40 mm and 100 mm in depth. The sensor node may weigh less than 1500 grams. The sensor node includes a printed circuit board, a communication module, and a sensor module enclosed in a weatherproof enclosure. "Sensor node" refers to a device or apparatus configured as recited in one or more of claims of this disclosure. In particular, a sensor node is a lightweight, compact device configured to include its own power source(s) and to communicate measurement data over a wireless communication channel to a host. "Sensor module" refers to a device, component, circuit, system, chip, or circuitry configured to detect and/or measure one or more characteristics of matter. A sensor module, in one embodiment, detects and/or measures levels of certain elements and/or particulates in a gas or a gas mixture, including, but not limited to, air. "Gas" refers to any substance or combination of substances in a gaseous state of matter. Examples of a gas include, but are not limited to, ambient air, driven air, a gas of a single element like hydrogen, nitrogen, or the like, or a gas of a compound such as chlorine, nitrous oxide, or the like. Furthermore, as used herein gas refers to substances that are a pure composition of one or more elements as well as substances that include contaminants, both gaseous contaminants and particulate contaminants. The modularity of the sensor node enables it to be configured differently depending on deployment scenarios to ensure scalable deployment of a dense sensor network in a region where air quality is measured.

The sensor node printed circuit board includes a controller that collects data from the sensor module and sends it to a data management platform using the communication module, and a power module that manages power delivery, battery charging and power monitoring. The communication module may interface with the sensor node printed circuit board via mini PCIe interface and may use any wireless technology including but not limited to WiFi, LTE, LoRa™, and narrowband IoT (NB-IoT) to send data from the sensor node to the data management platform.

The sensor module may interface with the sensor node printed circuit board via wire to board connectors. The sensor module includes a plurality of air quality sensors, which may measure the concentration of air pollutants. The sensor module may include at least one air quality sensor with an active sampling mechanism, such as a fan or a blower. The structure of the sensor module and the placement of the air quality sensors within the sensor module may be configured in such a way that the active sampling mechanism of one of the air quality sensors is used to expose all air quality sensors in the sensor module to samples of air from the ambient environment.

The sensor module may store instructions to measure the concentration of several air pollutants through several air quality sensors. The sensor node may be further configured to acquire air quality measurements, communicate air quality measurements to a data management platform, and receive configurations from a data management platform. The communication between sensor node and data management platform may be through a data network that is configured in a secure way and with low data overhead.

In further embodiments, a solar panel is mounted to the front of the sensor node through a gimbal fastener. The gimbal fastener may be oriented to maximize the exposure of the solar panel to direct sunlight. In certain embodiments, a user or technician may orient the solar panel in the field by adjusting the gimbal fastener. The solar panel may be coupled to the power module within the sensor node through a connector.

Hyperlocal air quality monitoring may include multiple sensor nodes deployed in a region. The system may include sensor nodes that are deployed in close proximity to highly accurate monitors found in the region. The system includes a data management platform that is configured to receive and process air quality measurements acquired by the sensor nodes and the monitors, identify co-location pairs as pairs of sensor nodes and monitors that are in close proximity to each other, create calibration profiles by calibrating the sensor nodes against the co-located monitors, correct measurements from sensor nodes according to the calibration profiles, store information in storage media and make information stored in storage media available to data consumers through data interfaces.

The system may include a method to identify co-location pairs as pairs of sensor nodes and monitors that are deployed in close proximity to each other, and to calculate calibration profiles by calibrating the sensor nodes against the co-located monitors. Other sensor nodes may have their measurements corrected by applying a calibration profile.

FIG. 1 is a high-level block diagram of a system 1 that may include a sensor node 100 according to certain embodiments of the disclosed subject matter. The sensor node 100 may comprise a communication module 102, a controller 104, a power module 106, a primary power source 108, a secondary power source 110, a reliable power supply 112, an input/output connector 114, an enclosure 116, a printed circuit board 200, and an interchangeable sensor module 600.

The communication module 102 may be configured to establish a wireless communication channel 122 over a network 118 of system 1 with a host 120 of system 1. "Host" refers to any computing device or computer device or computer system configured to send and receive commands. Examples of a host include, but are not limited to, a computer, a laptop, a mobile device, an appliance, a virtual machine, an enterprise server, a desktop, a tablet, a main frame, and the like. "Wireless communication channel" refers to a communication media configured to exchange information in the form of structured data between a sender and a receiver. A wireless communication channel includes a communication channel for which one or more of the links in the channel is between two components that are not connected by an electrical conductor. One example of a wireless communication technology is radio waves, but other forms of electromagnetic waves may be used. ("Wireless." Wikipedia. Sep. 9, 2019. Accessed Sep. 9, 2019. https://en.wikipedia.org/wiki/Wireless.)

Figure 13:
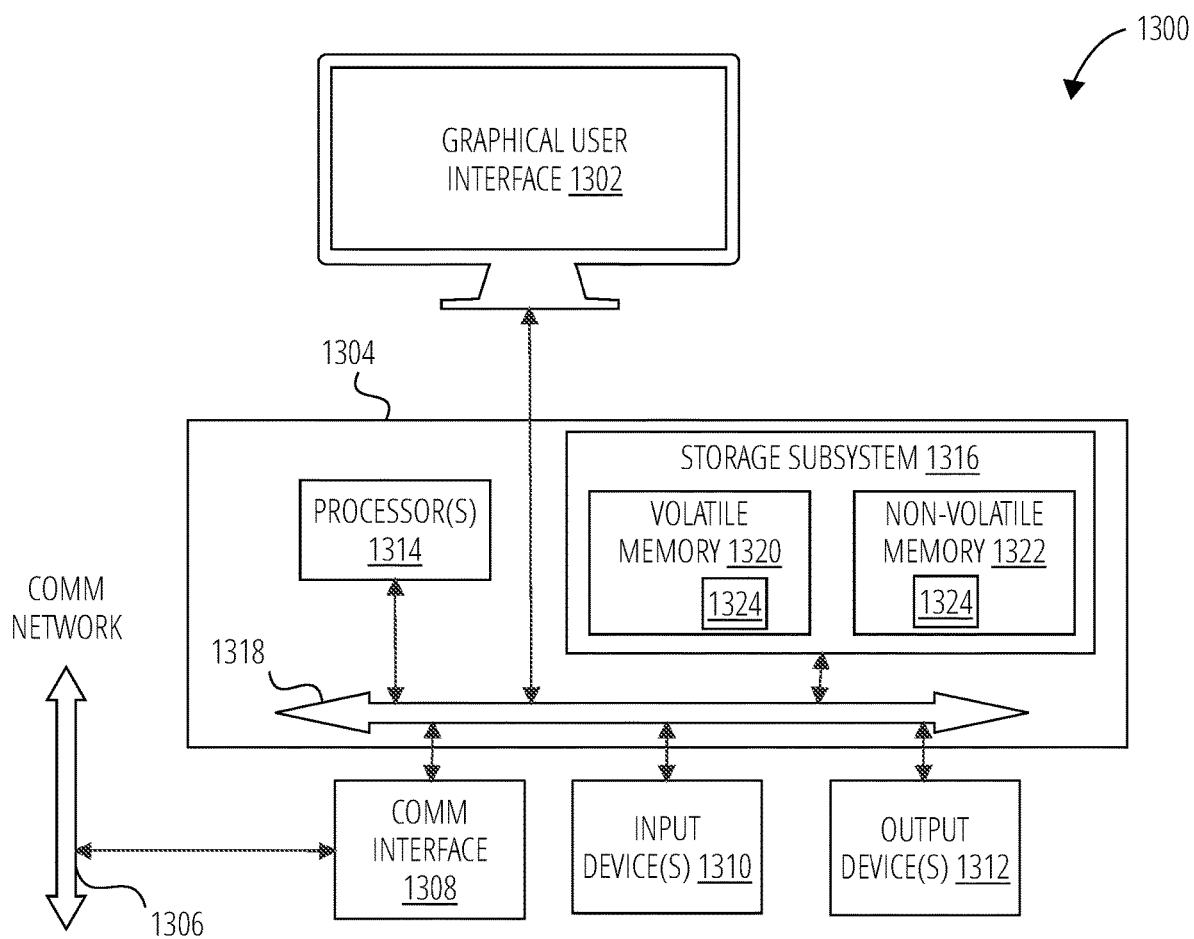
FIG. 13 is an example block diagram of a computing device 1300 that may incorporate certain embodiments.

The network 118 may be a communication network 1306 and the host 120 may be a computing device 1300 as illustrated in FIG. 13. The communication module 102 may further be configured to receive instructions from a data management platform to operate a sensor module. In one embodiment, the data management platform is operating on a host 120. The communication module 102 may receive a command to operate the sensor module per the instructions and may send a reading to the data management platform.

The controller 104 may be configured to manage the interchangeable sensor module 600 and send measurement data 124 to the host 120 by means of the wireless communication channel 122. "Controller" refers to any hardware, device, component, element, circuitry, or circuit configured to manage and control another software, hardware, firmware, or logic unit, component, device, or component. The controller 104 may store instructions to operate the interchangeable sensor module 600. The controller may receive a first current from a power source and may then operate the interchangeable sensor module 600 in response to a command.

The interchangeable sensor module 600 may be atmospherically isolated from the communication module 102 and the controller 104. This may be accomplished though O-rings or other seals surrounding openings in the body of the interchangeable sensor module 600. Holes necessary to mount or otherwise affix the interchangeable sensor module 600 within the sensor node 100 may be similarly sealed or located on tabs on the periphery of the interchangeable sensor module 600, such that the holes do not cause an incursion into the body of the interchangeable sensor module 600.

The interchangeable sensor module 600 may comprise one or more air quality sensors. The interchangeable sensor module 600 may receive a second current from the power source and may operate a fan utilizing the second current in response to the command to direct an aerosol stream, such as a gas, from an ambient environment external to an inlet port, to the one or more air quality sensors, and out of an outlet port. The interchangeable sensor module 600 may operate each of the one or more air quality sensors to generate a series of measurements before, during, or after operation of the fan and may generate the reading for each of the one or more air quality sensors from the series of measurement. The reading may then operate the data management platform to generate a measurement by selecting a co-location pair for the sensor node based on a location of the sensor node, determining a calibration model from the co-location pair, and generating the corrected measurement by applying the calibration model to the reading, the data management platform storing the reading and the corrected measurement. "Co-location pair" refers to a pair of sensors comprising at least one sensor node and one reference monitor positioned within a distance limit from each other. The distance limit is defined such that, if the distance between a reference monitor and a sensor node is at or less than the distance limit, the reference monitor and the sensor node are considered to be exposed to the same concentration of gas(es) and/or gas pollutants such as air pollutants.

The power module 106 may be configured to supply a reliable power supply 112 from a primary power source 108, such as a solar panel, supplemented by a secondary power source 110, such as a battery. The battery may be rechargeable, such that while enough power is available from the primary power source 108, the secondary power source 110 or battery may be recharged, storing the excess solar energy for later use. "Power module" refers to any hardware, device, component, chip, element, circuitry, or circuit configured to manage how much electrical power is provided to a circuit, circuitry, system, or subsystem. In one embodiment, a power module is a circuit of electrical components organized and housed within a single chip or other electrical component. In one embodiment, the power module is configured to constantly monitor current and/or voltage use and automatically connect a battery when the current and/or voltage used by a connected circuit drops below a threshold level. In one embodiment, the power module is configured to automatically charge a connected battery when the current and/or voltage supplied by a primary power source exceeds the current and/or voltage drawn by a connected circuit. In one embodiment, the power module may include a battery charger with power path management such as those available from Microchip Technology Inc. of Chandler Ariz. and may include other components such as a buck-boost converter, a battery monitor, and the like. "Power source" refers to a source of electrical energy for one or more electrical circuits connected to the power source. "Reliable power supply" refers to electrical energy converted from electrical potential energy at a specific rate per unit of time that is maintained at the specific rate per unit of time within an acceptable tolerance level for proper operation of one or more electrical circuits connected to the reliable power supply and which electrical circuits provide an electrical load. "Primary power source" refers to a power source for one or more electrical circuits that an electrical design of the one or more electrical circuits expects to be available a majority of the time and is designed to provide a majority of the electrical energy used by the one or more electrical circuits. "Secondary power source" refers to a power source for one or more electrical circuits that an electrical design of the one or more electrical circuits expects to be available less than a majority of the time and is expected to provide less than a majority of the electrical energy used by the one or more electrical circuits.

A printed circuit board 200 may be configured to interconnect the communication module 102, controller 104, and power module 106. The printed circuit board 200 may also comprise an input/output connector 114 configured to permit an interchangeable sensor module 600 to be coupled to the printed circuit board 200 for ease of maintenance, repair, or upgrade. Additional information regarding the printed circuit board 200 is provided with regard to FIG. 2. The interchangeable sensor module 600 is described in more detail with regard to FIG. 6.

An enclosure 116 may be configured to have walls forming an enclosed space, the walls having an inlet and an outlet aligned with inlet and outlet ports of the interchangeable sensor module 600. The enclosure 116 may house the printed circuit board 200, the interchangeable sensor module 600, and all other sensors and associated components, providing protection from environmental conditions as well as providing an isolated internal environment to facilitate accurate sensor readings. The modularity of the sensor node may enable the sensor node to be configured differently depending on deployment scenarios to ensure scalable deployment of a dense sensor network in a region where air quality is measured.

FIG. 2 illustrates a printed circuit board 200 in accordance with one embodiment. The printed circuit board 200 may comprise a DC power input 202, an input protection 204, a current sensor 206, a power management circuit 208, a battery 210, a battery monitor 212, a buck-boost converter 214, a controller 104, a magnetic buzzer 216, a communication module 102, a SIM interface 218, an antenna 220, and a sensor module printed circuit board 700.

Those skilled in the art may realize that the DC power input 202, input protection 204, current sensor 206, power management circuit 208, battery 210, battery monitor 212, buck-boost converter 214, and other components such as low-dropout regulators may be used to realize the power module 106 illustrated in FIG. 1.

The power management circuit 208 may be configured to monitor an electrical load and maintain the reliable power supply by selectively supplying supplemental power from the secondary power source, such as the battery 210, in response to the primary power source, such as a wired power supply 224 or solar power module 222, supplying power below a threshold. "Wired power supply" refers to a power source that provides power by way of an electrical conductor. In one example embodiment, a wired power supply is an alternating current available over a power grid for a community or city delivered over a power network, which is converted to a direct current power supply by a wired power supply component such as an AC power adapter.

The power management circuit 208 may also be configured to charge the battery 210 from the DC power input 202 when enough power is available. In some embodiments, primary power may be supplied by the battery. Solar power may function as a secondary power source to recharge the battery.

Those skilled in the art may also realize that the controller 104 may be a microcontroller (MCU) that may control the power module, receive and process a plurality of statuses and measurements from the power module, and communicate with the interchangeable sensor module 600, the communication module 102 and other external hosts through various serial communication protocols. Means of connection to external hosts may include a programming header, a debugging header, reset control, a SIM interface 218, and an antenna 220.

The device may provide audible feedback when it is set up and/or connected to the network. This audible feedback may be provided by means of a magnetic buzzer 216 powered by the power module and controlled by the controller 104. The device may provide audible notifications indicating that it has successfully powered on, that it has successfully connected to a network, that it has failed to connect with the network, and when its battery is low. Installation and configuration may in some embodiments be facilitated by interaction with an application available online, on a host device, or via a mobile application on a mobile device.

Figure 3:
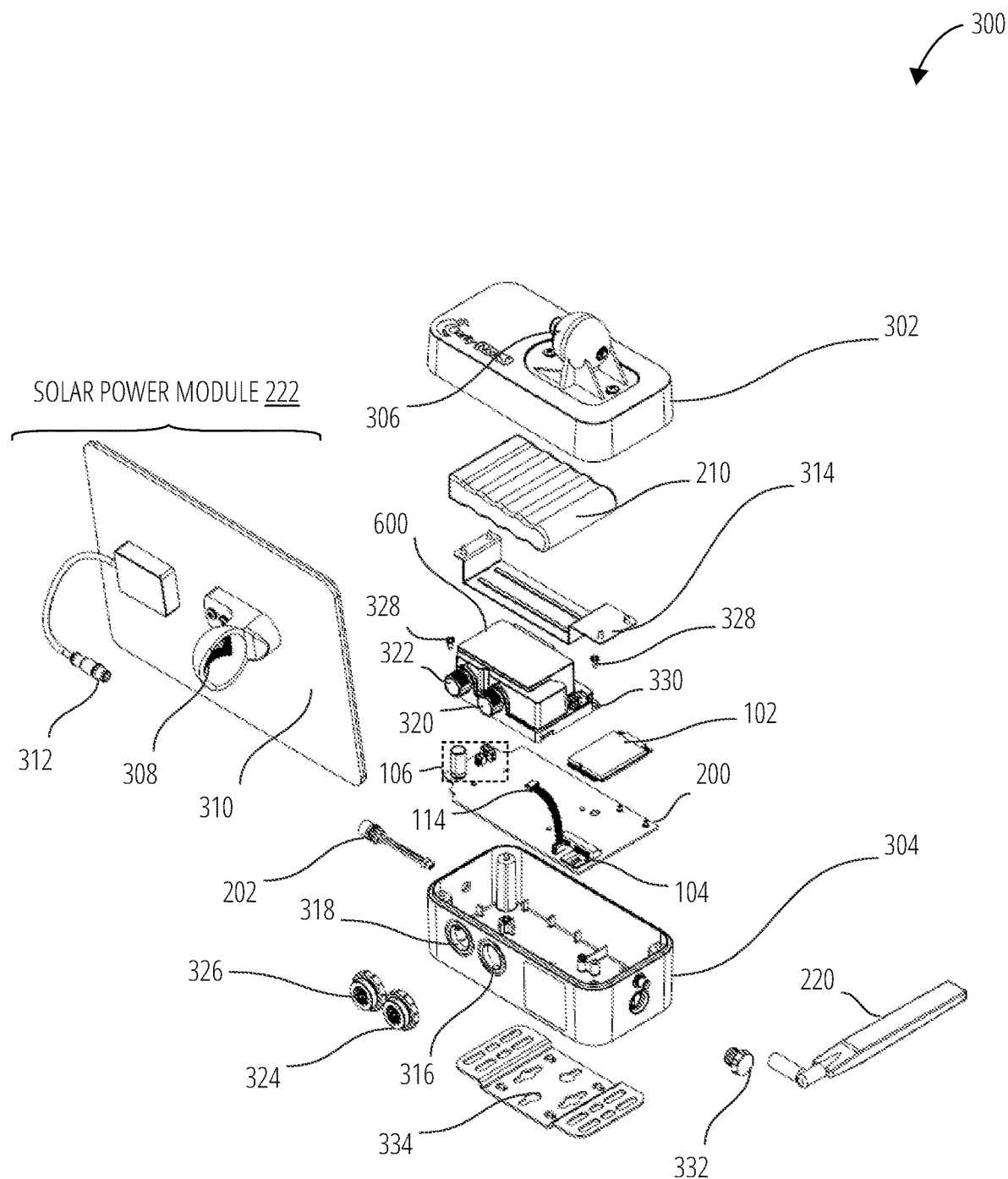
FIG. 3 illustrates an exploded view of an embodiment of a sensor node 300.

FIG. 3 illustrates an exploded view of a sensor node 300 in accordance with one embodiment. The sensor node 300 comprises an enclosure 116 that may be configured as an enclosure lid 302 and an enclosure body 304. The enclosure lid 302 may include a gimbal fastener 306 which engages a solar panel mounting structure 308 on a solar power module 222 in order to integrate the solar power module 222 with the system. The gimbal fastener 306 may allow for the orientation of the solar panel mounting structure 308 to be adjusted such that maximum exposure of the solar panel 310 to direct sunlight is achieved. Such an adjustment may be made by the installer or by a user at the location where the sensor node 300 is installed.

Figure 2:
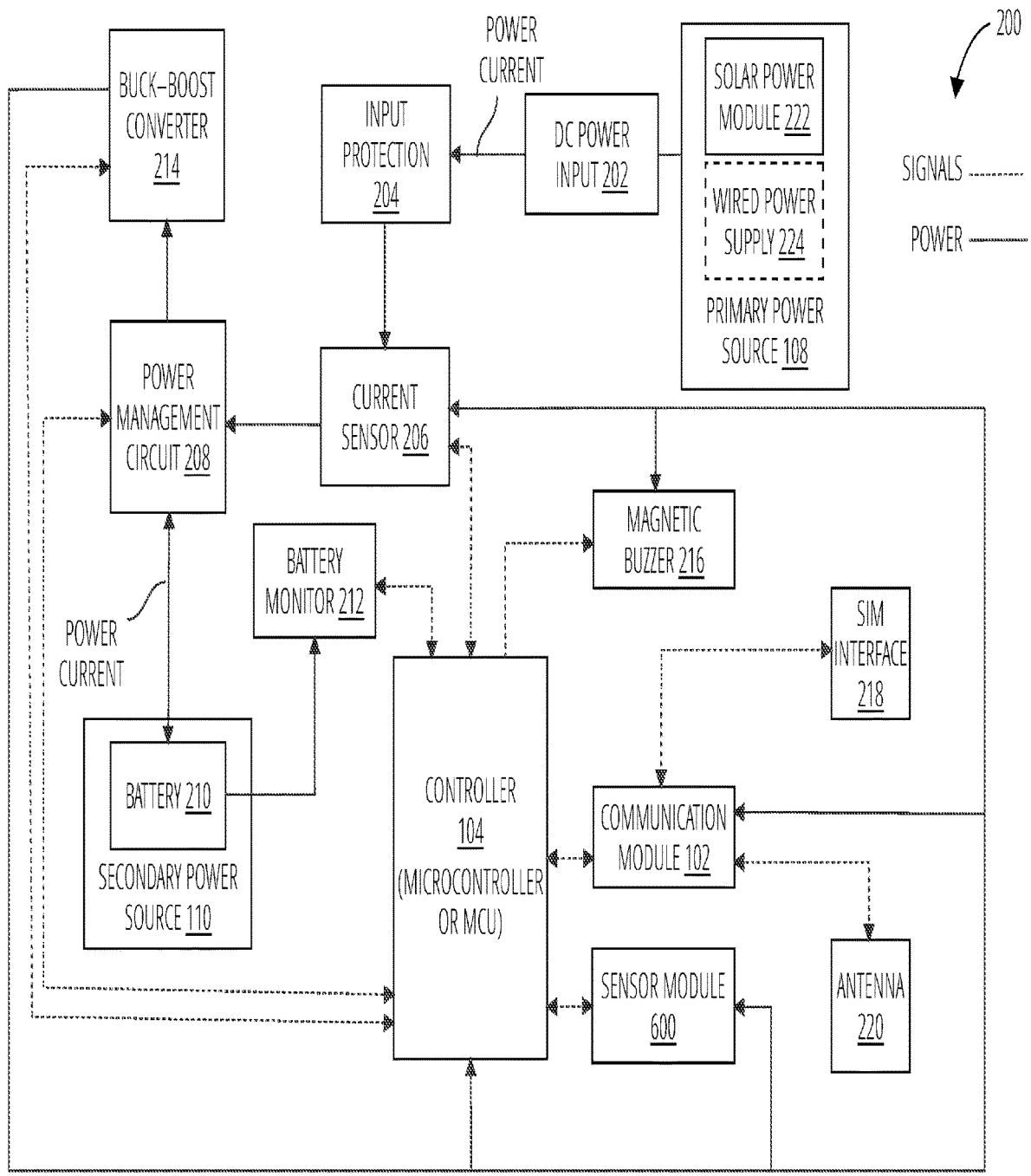
FIG. 2 illustrates a diagram of an embodiment of a printed circuit board 200.

The solar power module 222 may provide primary power to the printed circuit board 200, as discussed in detail with regard to FIG. 2, by connecting to the power module 106 of the printed circuit board 200 by means of a solar panel electrical coupling 312 connected to the DC power input 202. Additional, secondary power may be provided by a battery 210, secured in the enclosure 116 with a battery mount 314. The enclosure may also in some embodiments comprise a separate battery compartment. Some embodiments may include an AC power connection in addition to or instead of either or both of the solar power module 222 and battery 210.

The printed circuit board 200 may be configured as an interface between the communication module 102, controller 104, power module 106, and interchangeable sensor module 600 as described with regard to FIG. 1 and FIG. 2. The communication module 102 may send data to an external host by means of the antenna 220.

The enclosure body 304 may be configured with a first opening 316 and a second opening 318, sized and positioned to align with the inlet port 320 and outlet port 322 of the interchangeable sensor module 600, respectively. The openings may allow airflow to reach the interchangeable sensor module 600 through an inflow filter 324 and an outflow filter 326. The first opening 316 and inflow filter 324 may receive air samples from the environment. After the air sample has been processed through, for example, the interchangeable sensor module 600 the air sample may be returned to the environment through the second opening 318 and the outflow filter 326. The interchangeable sensor module 600 may attach to the printed circuit board 200 by means of removable fasteners 328 placed through holes 330 for removable fasteners incorporated into the body of the interchangeable sensor module 600.

The enclosure body 304 may also be configured with a vent 332. A node mount 334 may attach to the enclosure body 304, allowing the sensor node 300 to be mounted to a structure using the node mount 334. The node mount 334 may include a plurality of mounting holes for screws, nuts, bolts, or other fastening devices.

Figure 4:
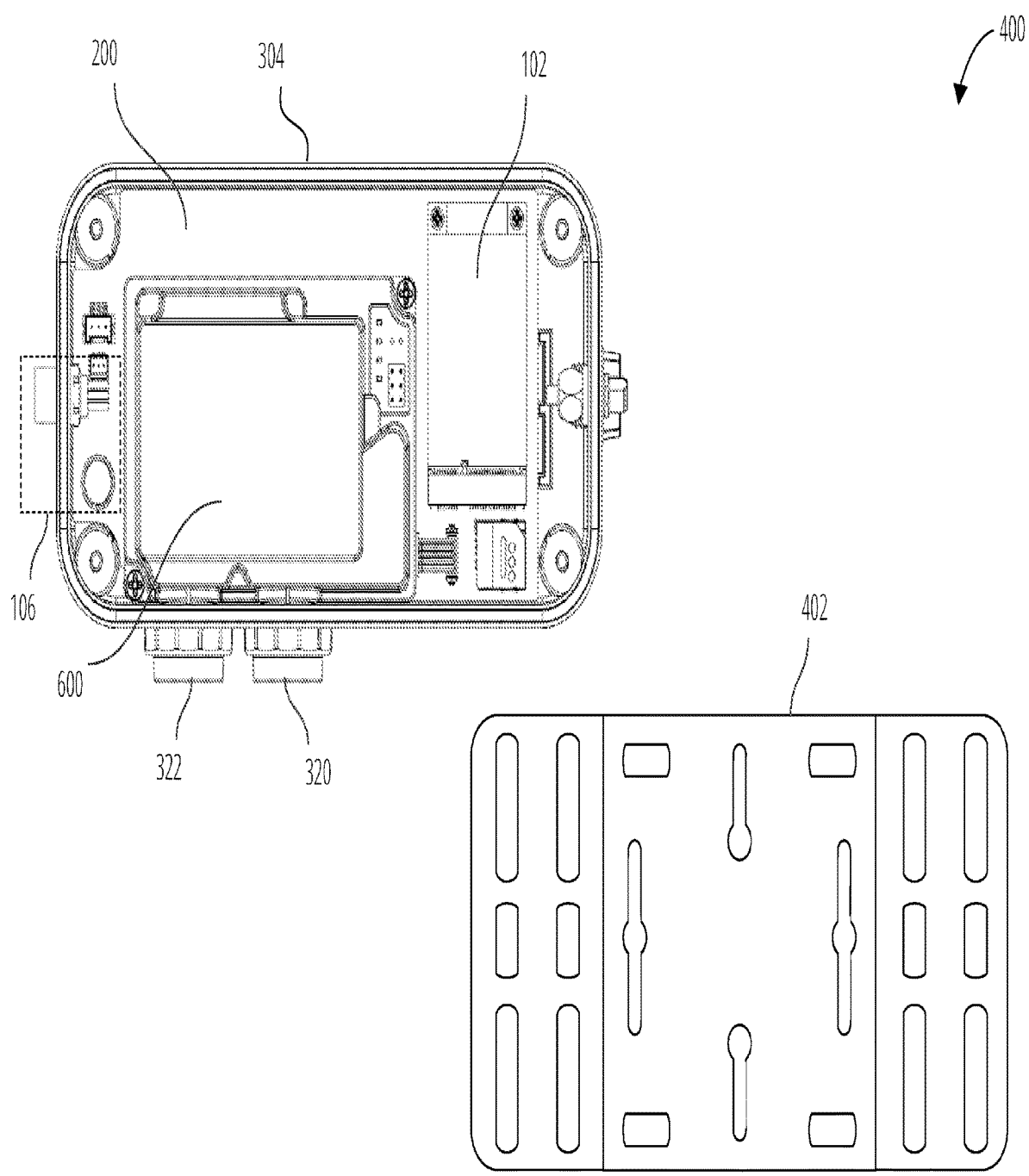
FIG. 4 illustrates a top view of a sensor node 400 in accordance with one embodiment.

FIG. 4 illustrates a top view of a sensor node 400 with the enclosure lid 302 removed, in accordance with one embodiment. The sensor node 400 comprises an enclosure body 304 that encompasses an interchangeable sensor module 600 and a printed circuit board 200 that includes a communication module 102, a power module 106 and a controller. The sensor node 400 may additionally comprise a universal mount 402 configured to mount the enclosure body 304 in a plurality of mounting configurations. "Universal mount" refers to a plate, bracket or the like configured with one or more holes and/or one or more slots arranged and sized to accept one or more fasteners to secure the mount to a wall, fence, or pole and to secure a sensor node to the universal mount.

The printed circuit board 200 with communication module 102, controller, and power module 106, may be substantially the same as those illustrated in FIG. 1 and FIG. 2. The power module 106 may be configured to accept power from a solar power module that may supply current as a primary power source. The power module 106 may also be configured to accept power from a battery configured to selectively supply current as a primary power source and/or to supplement power supplied by the solar power module.

The interchangeable sensor module 600 may be configured to monitor an air sample for one or more characteristics, such as air quality or concentrations of specific gases or particulates. "Characteristic" refers to any property, trait, quality, or attribute of an object or thing. ("characteristic" Merriam-Webster.com. Merriam-Webster, 2019. Web. 27 Aug. 2019.) Examples of characteristics include, but are not limited to, chemical composition, water content, temperature, relative humidity, particulate count, contaminant count, and the like.

The interchangeable sensor module 600 may comprise an inlet port 320 and an outlet port 322. In some embodiments, the interchangeable sensor module 600 may be an air quality sensor. Air quality sensors may comprise an airflow structure, a particle counter, and at least one other air quality sensor. Such a sensor module may form an airflow structure to direct an aerosol stream to the at least one other air quality sensor before directing the aerosol stream to the particle counter. See FIG. 6 for additional detail.

The enclosure body 304 may be configured with openings sized and positioned to align with the inlet port 320 and outlet port 322 of the interchangeable sensor module 600, respectively. The openings may allow airflow to reach the interchangeable sensor module 600 through an inflow filter and an outflow filter. The inlet port 320 may receive air samples from the environment through the opening in the enclosure body 304 and the inflow filter. After the air sample has been processed through, for example, the interchangeable sensor module 600, the air sample may be returned to the environment through the outlet port 322 through the opening in the enclosure body 304 and the outflow filter.

In addition to the enclosure body 304 and the enclosure lid 302 (shown in FIG. 3), the enclosure 116 comprising the enclosure lid 302 and enclosure body 304 may also comprise one or more seals. The enclosure lid 302 may fasten to the enclosure body 304 by means of removable fasteners. "Removable fastener" refers to any fastener configured to be removed using conventional tools such as a screwdriver, a wrench, a nut driver, or the like. Removable fasteners may be made of a variety of materials including metal, plastic, composite materials, metal alloys, plastic composites, and the like. Examples of removable fasteners include, but are not limited to screws, bolts, nuts, posts, pins, thumb screws, and the like.

The seals, openings, and enclosure lid 302 may be configured to engage the enclosure body 304 to provide a liquid ingress protection rating greater than four. "Ingress protection rating" refers to a rating system that defines the level that an enclosure protects internal components from ingress of solid objects, liquids, and gases. Engineering ToolBox, (2003). IP—ingress protection rating. [online] Available at: https://www.engineeringtoolbox.com/ip-ingress-protection-d_452.html 5 Sep. 2019. In this manner, the electronics within the sensor node 400 may be isolated and protected from environmental conditions. In another embodiment, the electronics of the sensor node 400 may be isolated from the air sample chambers such that only the air sample chambers are exposed to a gas mixture sample.

In another embodiment, the enclosure may comprise a body and a lid, wherein the lid is permanently connected to the body. In this embodiment, the enclosure may comprise an opening and a door configured to seal the opening from moisture ingress when the door is closed. This opening may be sized to slidably accept the interchangeable sensor module 600.

In some embodiments, the sensor node 400 may further comprise a second interchangeable sensor module configured to monitor one or more environmental characteristics. The second interchangeable sensor module may be configured to sit within the enclosure and may removably couple to the controller and the power module.

Figure 5:
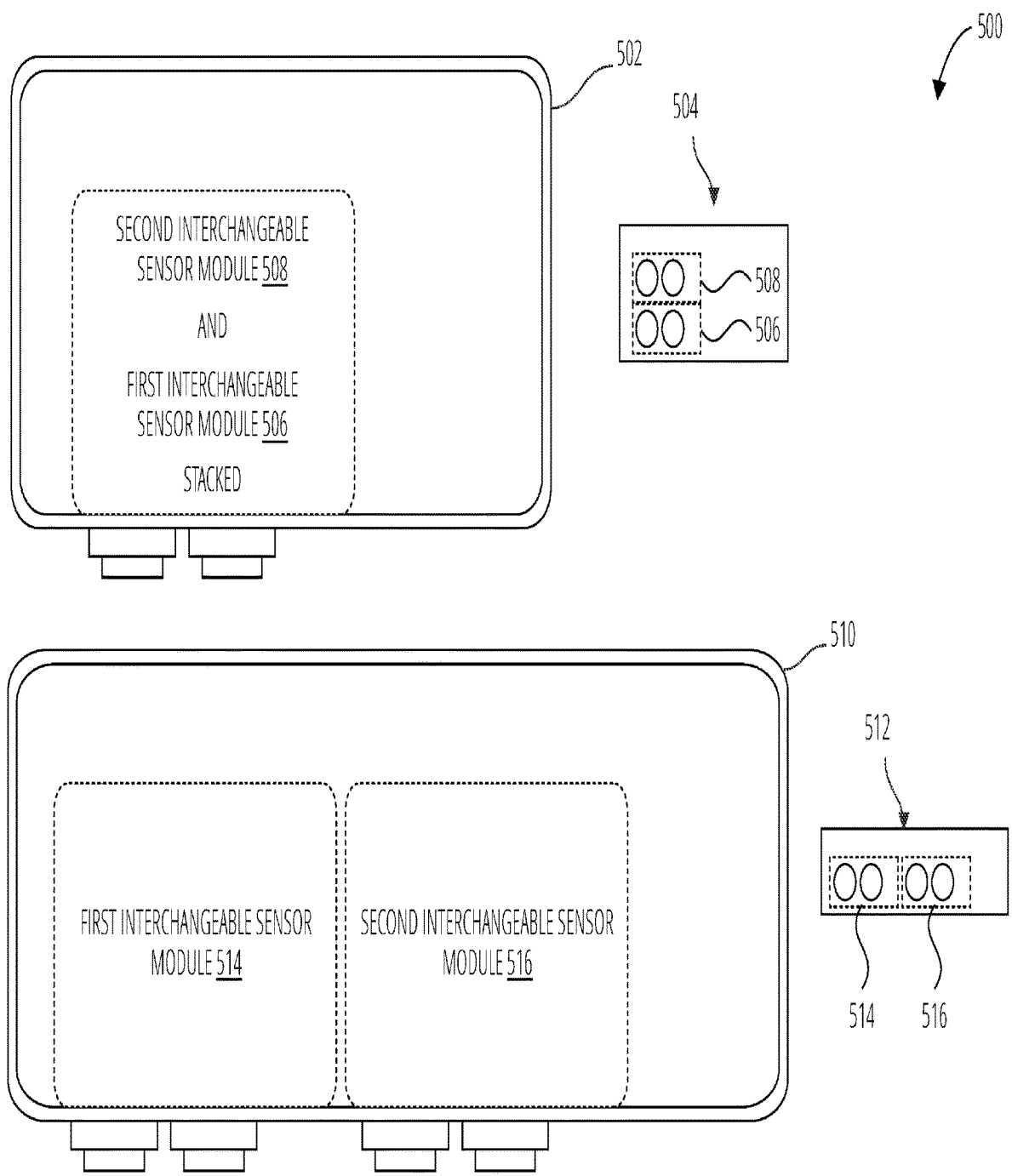
FIG. 5 illustrates a dual sensor module configuration 500 in accordance with one embodiment.

FIG. 5 illustrates dual sensor module configuration 500 in accordance with some embodiments. The sensor node may comprise an enclosure configured to accommodate two interchangeable sensor modules.

A top view of an enclosure for two stacked sensor modules 502 is shown with dotted lines indicating the footprint that a stacked first interchangeable sensor module 506 and second interchangeable sensor module 508 would occupy within the enclosure. A side view of an enclosure for two stacked sensor modules 504 is also illustrated, showing the second interchangeable sensor module 508 stacked atop the first interchangeable sensor module 506. This is one embodiment, and is not intended to limit the possible configurations.

A top view of an enclosure for two side-by-side sensor modules 510 is also shown, along with a side view of an enclosure for two side-by-side sensor modules 512. Both enclosures 510/512 are configured to house a first interchangeable sensor module 514 and a second interchangeable sensor module 516 arranged side by side. This is one embodiment, and is not intended to limit the possible configurations.

Figure 6:
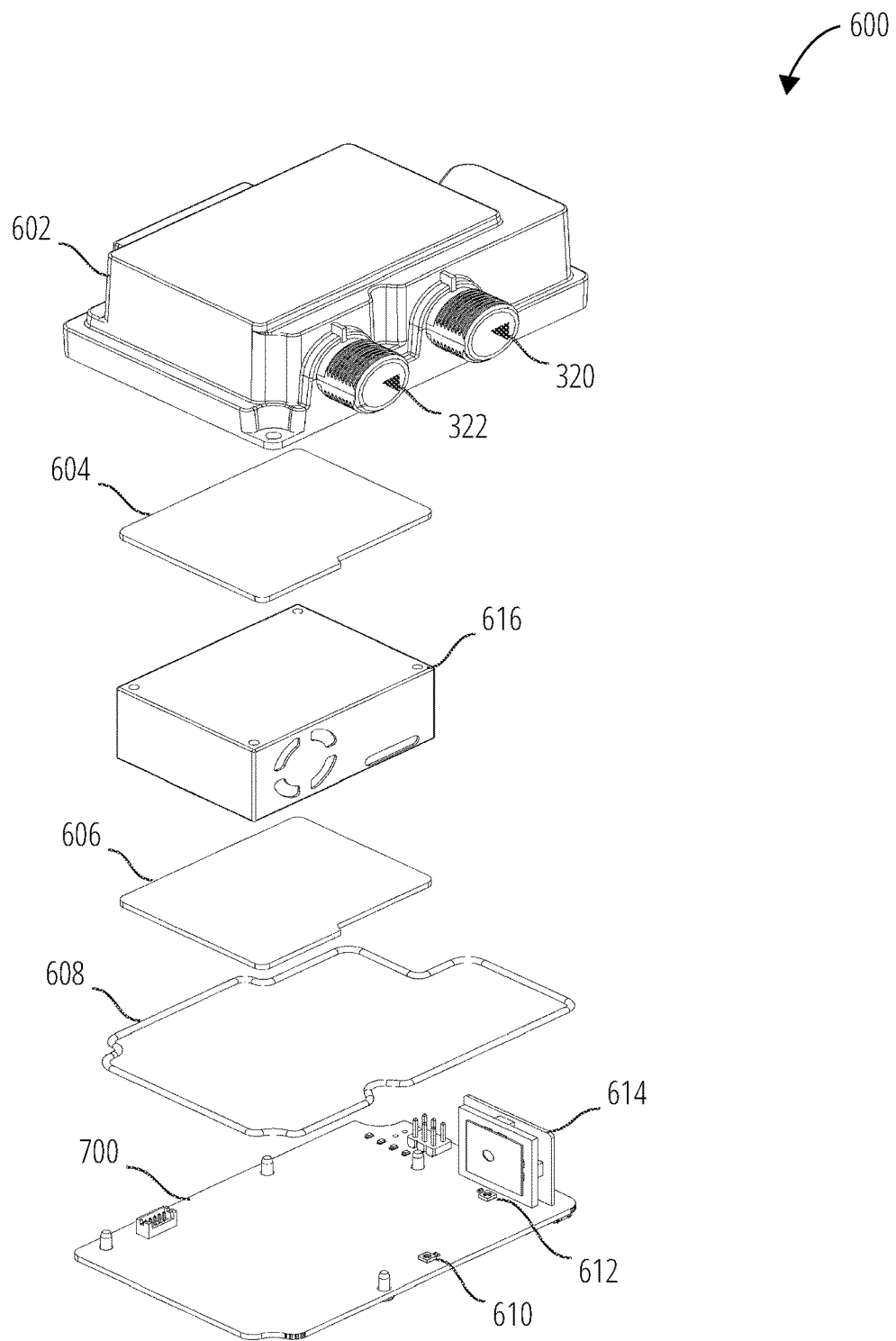
FIG. 6 illustrates an exploded view of an embodiment of an interchangeable sensor module 600.

FIG. 6 illustrates an interchangeable sensor module 600 in accordance with one embodiment. "Interchangeable sensor module" refers to a sensor module specifically designed to be removed from a larger unit, system, subsystem, or the like. In certain embodiments, the interchangeable sensor module includes one or more holes or openings each configured to receive a removable fastener such as a screw, a bolt, a pin, or the like. In certain embodiments, the interchangeable sensor module includes one or more clips, tabs, slots, or other structural components configured to engage corresponding structural components of a housing or bracket of a larger system or subsystem, such that the interchangeable sensor module is configured to engage and disengage with the housing or bracket to install or remove the interchangeable sensor module. The interchangeable sensor module 600 comprises an airflow structure 602, an inlet port 320, an outlet port 322, a top buffer 604, a bottom buffer 606, an O-ring 608, a sensor module printed circuit board 700, a sensor 610, a sensor 612, a sensor 614, and a particle counter 616.

The airflow structure 602 may be airtight with the help of the O-ring 608 such that any air samples are fully contained and analyzed within the airflow structure 602. The interchangeable sensor module 600 may include at least one air quality sensor with an active sampling mechanism, such as a fan or a blower. The interchangeable sensor module 600 may include an inlet port 320 for drawing in the air sample and an outlet port 322 for expelling the sampled air.

The sensor module printed circuit board 700 may comprise and/or connect a plurality of electrical components configured to perform the sensing functions necessary to detect and analyze air quality conditions. The sensor module printed circuit board 700 is illustrated in more detail in FIG. 7.

The interchangeable sensor module 600 may include a plurality of air quality sensors such as a sensor 610, a sensor 612, and a sensor 614, which may measure the concentration of air pollutants. These sensors may be located in the airflow structure 602 and mounted to the sensor module printed circuit board 700.

The structure of the interchangeable sensor module 600 and the placement of the air quality sensors within the interchangeable sensor module 600 may be configured in such a way that the active sampling mechanism of one of the air quality sensors is used to expose all air quality sensors in the interchangeable sensor module 600 to samples of air from the ambient environment.

The particle counter 616 may be sandwiched between the top buffer 604 and the bottom buffer 606 to reduce vibration and electrically isolate its metal chassis from the sensor module printed circuit board 700. The enclosure illustrated in FIG. 3 and FIG. 4 may be configured to atmospherically isolate the interchangeable sensor module 600 from the power module, communication module, and controller. The sensor node may include removable fasteners configured to engage the enclosure and the interchangeable sensor module 600.

A modular air sensor or gas sensor design may be employed, such that a range of sensor modules may be connected to each sensor node. Sensor modules may be easily installed, removed, and replaced for repair or upgrade, or may provide a range of sensor types to measure specific air components in specific locations. Such swappable sensor modules may connect to the sensor node PCB by means of a standard connector.

Figure 7:
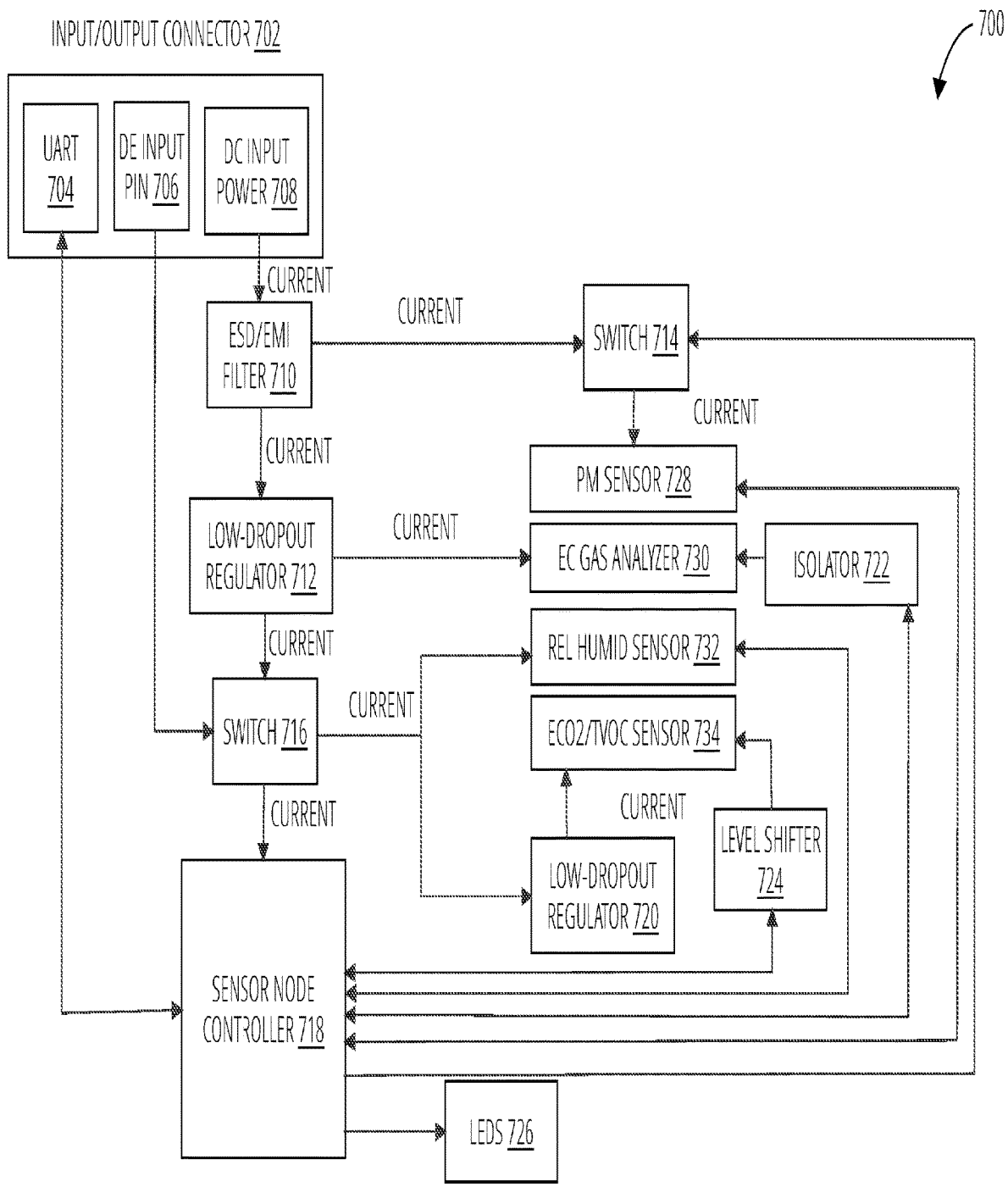
FIG. 7 illustrates a diagram of an embodiment of a sensor module printed circuit board 700.

FIG. 7 illustrates a sensor module printed circuit board 700 in accordance with one embodiment. The sensor module printed circuit board 700 may comprise an input/output connector 702, a universal asynchronous receiver/transmitter 704, a digital enable input pin 706, a DC input power 708, an electrostatic discharge and electromagnetic interference filter 710, a low-dropout regulator 712, a switch 714, a switch 716, a sensor node controller 718, a low-dropout regulator 720, an isolator 722, a level shifter 724, light emitting diodes 726, a particulate matter sensor 728, an electrochemical gas analyzer 730, a relative humidity sensor 732, and an equivalent carbon dioxide and total volatile organic compounds sensor 734.

In another embodiment, a sensor module may contain multiple air quality sensors. Those skilled in the art may realize that the aforementioned components can be used to realize a sensor module that may gather sensor measurements from a plurality of sensors and send the sensor measurements to a host device (such as a sensor node) upon request via serial interface.

Figure 8:
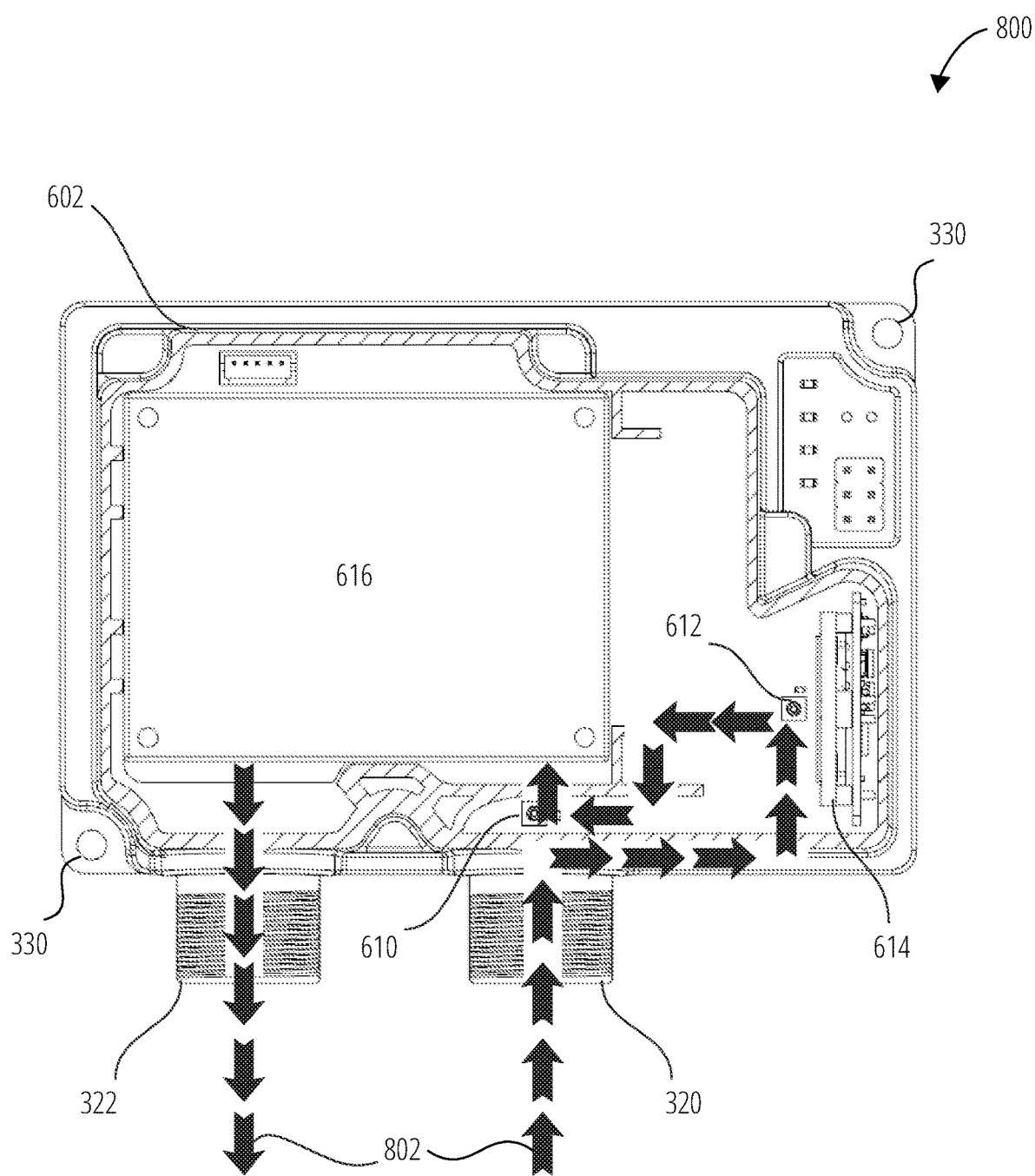
FIG. 8 illustrates a cross-sectional view of a sensor module 800 in accordance with one embodiment.

FIG. 8 illustrates a cross-sectional view of a sensor module 800 in accordance with one embodiment. The sensor module 800 comprises an airflow structure 602, an inlet port 320, an outlet port 322, a sensor 610, a sensor 612, a sensor 614, and holes 330 for removable fasteners.

The enclosure encompassing the sensor module 800 may be configured to atmospherically isolate the sensor module 800 from the power module, communication module, and controller. The holes 330 may be configured to accept removable fasteners such as screws to engage the enclosure and the holes 330. These holes 330 may be located on tabs which extend at the periphery of the interchangeable sensor module 600 body, and in this manner provide mounting holes that do not cause an incursion into the interchangeable sensor module 600 body, and thus do not need to be sealed to maintain atmospheric isolation of the sample being tested. Those of skill in the art will appreciate that other forms of connectors or fasteners other than holes 330 and/or removable fasteners for coupling the sensor module 800 to the enclosure.

To change out an interchangeable sensor module, a user may open the enclosure of the sensor node to access the sensor module 800. This may be accomplished by removing the enclosure lid in some embodiments. In other embodiments not illustrated, the enclosure may be configured with a sensor module aperture with a latched and sealed door, or some other configuration allowing access to the sensor module 800 while providing adequate isolation from the environment around the sensor node.

After accessing the sensor module 800, The user may remove the removable fasteners (e.g., screws, bolts, latches, or other fastening devices), thus releasing the sensor module 800 from mounting hardware incorporated into the enclosure or sensor node PCB. The user may attach a new interchangeable sensor module in place of the one removed, securing it by replacing the removable fasteners through the holes 330 located on the new sensor module. This is only one embodiment. Interchangeable sensor modules may alternatively incorporate captive fasteners that may be disengaged from the enclosure and/or sensor node PCB but remain attached to the sensor module. The sensor node may alternately include a latching mechanism holding interchangeable sensor modules in place when installed. Any combination of these methods may be used to secure the sensor module 800 in place within the sensor node while allowing easy changeout to facilitate repairs or upgrades.

An airflow path 802 is illustrated, using black arrows to show how air from the surrounding environment passes through the sensor module 800. The airflow may travel in through the inlet port 320 into a series of baffles designed into the airflow structure 602, configured to direct the air over at least one air quality sensor. In the illustrated embodiment, the air is directed across sensor 614, then passes over sensor 612. The air is then directed in the opposite direction to pass over sensor 610 before entering the particle counter 616. After passing through the particle counter 616, the air exits the airflow structure 602 and flows out through the outlet port 322.

In this manner, and due to the isolation provided by the airflow structure 602, as well as the O-ring 608, and the enclosure itself, the volume of air being sampled, tested, and analyzed, may remain isolated from the environment both inside and outside the enclosure.

Figure 9:
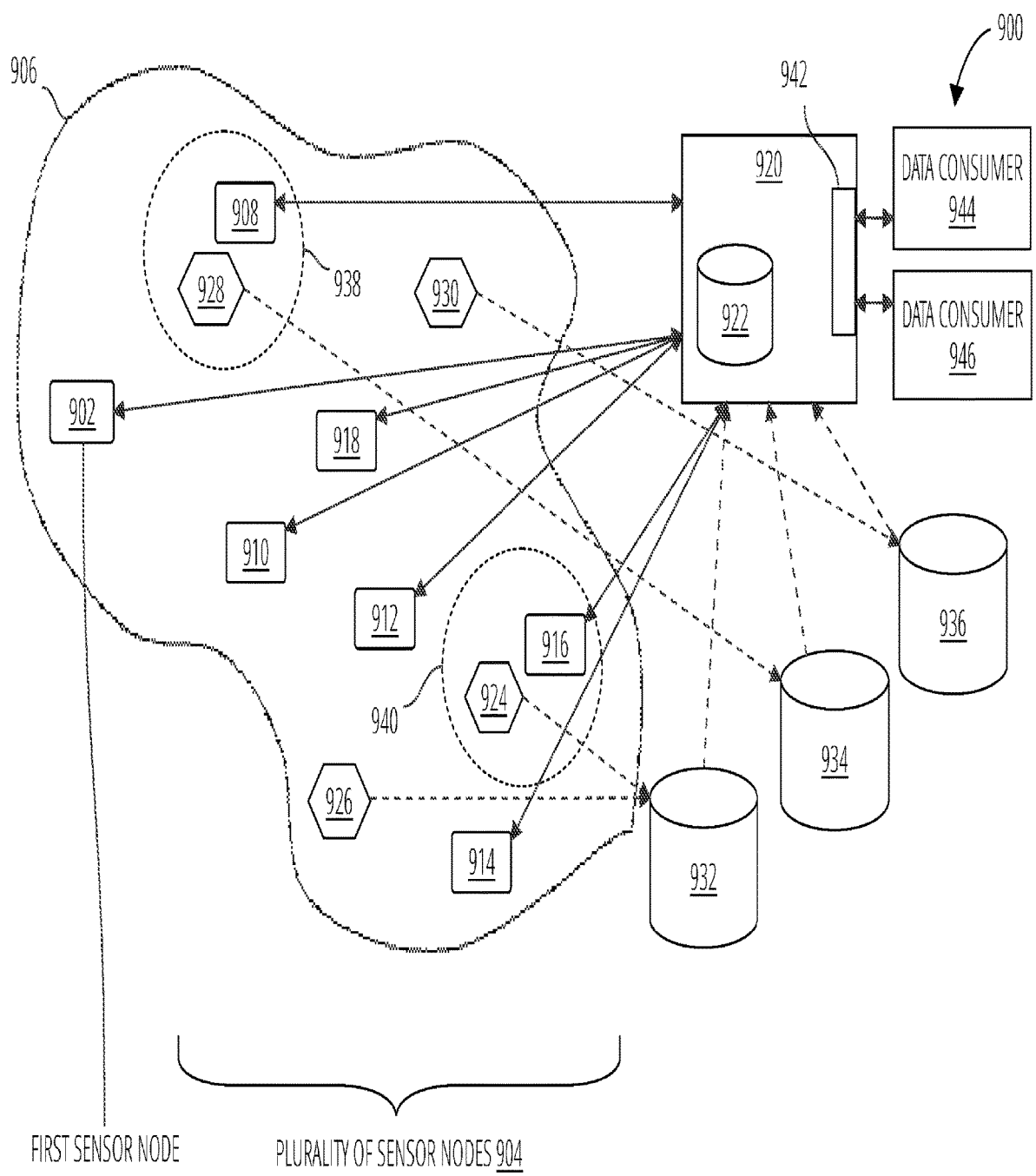
FIG. 9 illustrates an embodiment of a hyperlocal air quality monitoring system 900.

FIG. 9 is a system diagram illustrating a hyperlocal air quality monitoring system 900 deployed in a region 906 in accordance with certain embodiments of the disclosed subject matter.

The hyperlocal air quality monitoring system 900 may comprise a first sensor node 902, a plurality of sensor nodes 904, and a region 906. The plurality of sensor nodes 904 may comprise a sensor node 908, a sensor node 910, a sensor node 912, a sensor node 914, a sensor node 916, and a sensor node 918. The hyperlocal air quality monitoring system 900 may further comprise data management platform 920, a storage control memory structure 922, a reference monitor 924, a reference monitor 926, a reference monitor 928, a reference monitor 930, a data control memory structure 932, a data control memory structure 934, a data control memory structure 936, a co-location pair 938, a co-location pair 940, a data interface 942, a data consumer 944, and a data consumer 946. Any number of sensor nodes, monitors, data control memory structures, etc., may be utilized herein, and the number is not limited to the ones in FIG. 9.

The hyperlocal air quality monitoring system 900 may be configured to implement the method disclosed herein. A first sensor node 902 may be placed near a reference monitor 924 within a region 906. A plurality of sensor nodes 904 may then be placed at various locations within the region 906. Measurement data may be gathered from the first sensor node 902, the reference monitor 924, and the plurality of sensor nodes 904. A calibration profile may be determined for each of the first sensor node 902 and the plurality of sensor nodes 904 based on measurement data from the reference monitor 924. In one embodiment, the calibration profile may be determined for each of the first sensor node 902 and the plurality of sensor nodes 904 based on measurement data from the reference monitor 924 and measurement data from the first sensor node 902. The calibration profile for each of the first sensor node 902 and the plurality of sensor nodes 904 may be applied to measurement data from each of the first sensor node 902 and the plurality of sensor nodes 904 to obtain calibrated measurement data for each of the sensor nodes.

In one embodiment, the hyperlocal air quality monitoring system 900 deployed in region 906 may be composed of multiple sensor nodes (the first sensor node 902, the sensor node 908, the sensor node 910, the sensor node 912, the sensor node 914, the sensor node 916, and the sensor node 918) deployed at known locations within region 906 where it is desired to measure air quality, and a data management platform 920. The sensor nodes periodically acquire air quality measurements and communicate said measurements to the data management platform. The data management platform is configured to receive information from the sensor nodes and store it in a storage control memory structure 922. As a non-limiting example, the sensor nodes are low-cost air quality sensors that communicate air quality measurements to the data management platform 920 wirelessly through a data network, and the data management platform 920 is a combination of controllers, data processors, software services, control memory structures, and the like. As a non-limiting example, it is desired to measure the air quality at several outdoor locations in a city, and the sensor nodes are mounted at those locations to city furniture, building walls, or other infrastructure.

Reference monitors (a reference monitor 924, a reference monitor 926, a reference monitor 928, and a reference monitor 930) are found at known locations within region 906 and periodically acquire air quality measurements and publish said measurements to data control memory structures (a data control memory structure 932, a data control memory structure 934, and a data control memory structure 936). "Reference monitor" refers to a gas monitor such as an air monitor approved by a municipal, state, or other governmental agency for use in tracking the composition and make up of air in a given location. A reference monitor is calibrated and certified to provide measurement data that is accurate and reliable for determining a quality measure for air in the region serviced by the reference monitor.

The data management platform 920 is configured to periodically retrieve information from the data control memory structures and store it in the storage control memory structure 922. As a non-limiting example, the monitors are highly accurate air quality monitoring stations operated by governmental agencies or other organizations, with measurement accuracy that may be higher than the accuracy of the sensor nodes, and the data control memory structures are online data sharing platforms where governmental agencies or other organizations openly publish air quality monitoring information for divulgation with the public. The data management platform 920 is configured to perform processes aimed at increasing the accuracy of the measurements acquired by the sensor nodes.

Some sensor nodes may be purposefully deployed at close proximity to some monitors with the aim of increasing the accuracy of the measurements acquired by the sensor nodes. Pairs of sensor nodes and monitors with distance from each other that is below a distance limit are considered co-located and called co-location pairs (e.g., a co-location pair 938 and a co-location pair 940). Said distance limit is selected in such a way that, if the distance between a reference monitor and a sensor node is lower than the distance limit, the reference monitor and the sensor node may be considered to be exposed to the same concentration of air pollutants. As a non-limiting example, the sensor node 908 and the reference monitor 928 compose the co-location pair 938, and the sensor node 916 and the reference monitor 924 compose the co-location pair 940.

In one process, the data management platform 920 identifies the co-location pairs as a sensor node and a reference monitor with a distance from each other that is within a distance limit and compares for each co-location pair the measurements from the sensor node against the measurements from the reference monitor to perform a calibration of the sensor node against the reference monitor. The result of the calibration is a calibration profile, composed of calibration constants and calibration model. "Calibration profile" refers to a set of calibration constants and a calibration model. Sensor node measurements having minimal error in relation to reference monitor measurements are generated by applying the calibration constants to the sensor node measurements according to the calibration model. "Calibration constant" refers to a whole or rational number used in place of a variable in a formula for a calibration model. As a calibration model may have one or more calibration constants, various methods may be used to determine the values for the calibration constants. In one example, calibration constants are determined by fitting a calibration model to the measurement data from a sensor and a reference monitor of a co-location pair. "Calibration model" refers to a mathematical model for relating one or more random variables and one or more non-random variables and calibrating measurement data from a sensor to remove measurement error and bias. Examples of a calibration model include, but are not limited to, a linear model, and the like.

In one example embodiment, a calibration model for determining calibrated measurement data is represented by the formula calibrated_measurement=sensor measurement data*bias+offset, where the bias and offset comprise calibration constants. In another example embodiment, a calibration model for determining calibrated measurement data is represented by the formula calibrated_measurement=sensor measurement data*a+ temperature_measurement*b+humidity_measurement*c+d, where a, b, c and d comprise calibration constants. In another example embodiment, a calibration model for determining calibrated measurement data is represented by the formula calibrated_measurement=sensor measurement data^2*i+sensor measurement data*j+k, where i, j, and k comprise calibration constants.

The calibration constants applied to the sensor node measurements according to the calibration model generate sensor node measurements that minimize the error between the sensor node measurements and the reference monitor measurements for the sensor node and the reference monitor belonging to a co-location pair. Each calibration profile is stored in the storage control memory structure 922 by the data management platform 920. As a non-limiting example, the data management platform 920 identifies the co-location pair 938 and the co-location pair 940 and compares the measurements acquired by sensor node and the reference monitor measurements in each co-location pair to calculate calibration profiles, which may be composed of an offset coefficient and a bias coefficient as calibration coefficients, and a linear model as calibration model.

In another process, every time a reading from a sensor node is received, the data management platform 920 may select a calibration profile stored in storage control memory structure 922 and apply the calibration profile to correct the reading acquired by the sensor node and store the reading and the corrected measurement in the storage control memory structure 922. As a non-limiting example, the measurements from the first sensor node 902, the sensor node 908, the sensor node 910, the sensor node 918 are corrected according to the calibration profile calculated from the co-location pair 938, and measurements from the sensor node 912, the sensor node 914, and the sensor node 916 are corrected according to the calibration profile calculated from the co-location pair 940.

The data management platform 920 is configured to make the measurements and the measurements stored in the storage control memory structure 922 may be sent via a data interface 942 to a data consumer 944 and a data consumer 946. In one non-limiting example, the data consumer 944 and the data consumer 946 are applications that enable the application user to display and download the air quality measurements taken by the sensor nodes at locations within the region 906 where it is desired to measure the air quality.

Figure 10:
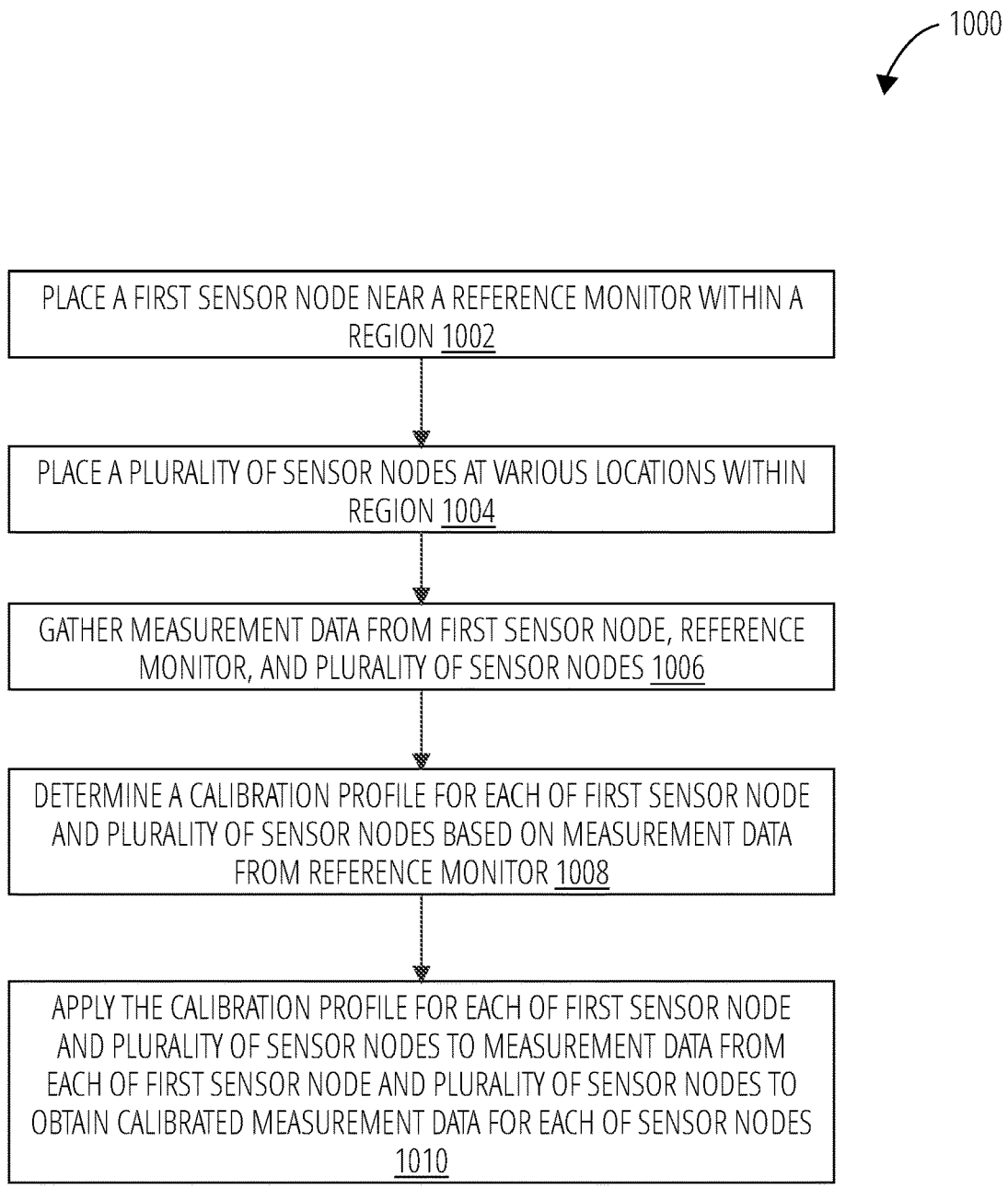
FIG. 10 illustrates a routine in accordance with one embodiment.

FIG. 10 illustrates an operation method 1000 in accordance with one embodiment. This method may employ a system such as that described with respect to FIG. 9.

In block 1002, operation method 1000 may place a first sensor node near a reference monitor within a region. In block 1004, operation method 1000 may place a plurality of sensor nodes at various locations within the region. In block 1006, operation method 1000 may gather measurement data from the first sensor node, the reference monitor, and the plurality of sensor nodes.

In block 1008, operation method 1000 may determine a calibration profile for each of the first sensor node and the plurality of sensor nodes based on measurement data from the reference monitor. In block 1010, operation method 1000 may apply the calibration profile for each of the first sensor node and the plurality of sensor nodes to measurement data from each of the first sensor node and the plurality of sensor nodes to obtain calibrated measurement data for each of the sensor nodes.

In some embodiments, applying the calibration profile may comprise wirelessly communicating a calibration profile to each of the first sensor node and the plurality of sensor nodes. In some embodiments, determining a calibration profile may comprise determining a calibration model for the first sensor node and determining a set of calibration constants for the first sensor node. In some embodiments, applying the calibration profile may comprise applying the calibration model to measurement data for the first sensor node to generate calibrated measurement data.

To ensure high accuracy, precision and reliable operation on the field, each individual sensor node may undergo thorough calibration at the factory. The modular design of the sensor node may allow for scalable and parallel calibration. Calibration of deployed sensor nodes may comprise transmitting a calibration profile to each of the first sensor node and the plurality of sensor nodes. This calibration profile may be transmitted wirelessly, over a cloud network configuration or by some other means. To allow city wide deployment of hundreds of sensor node, and to enable real-time reaction to air pollution events, a first sensor node may be collocated with government reference equipment for the entire duration of a monitoring project. Data from the government reference equipment may be used to calibrate data from the first sensor node, by allowing computation of bias and offset calibration constants. These computed bias and calibration constants may be applied in real-time to the plurality of sensor nodes across the entire sensor network.

Figure 11:
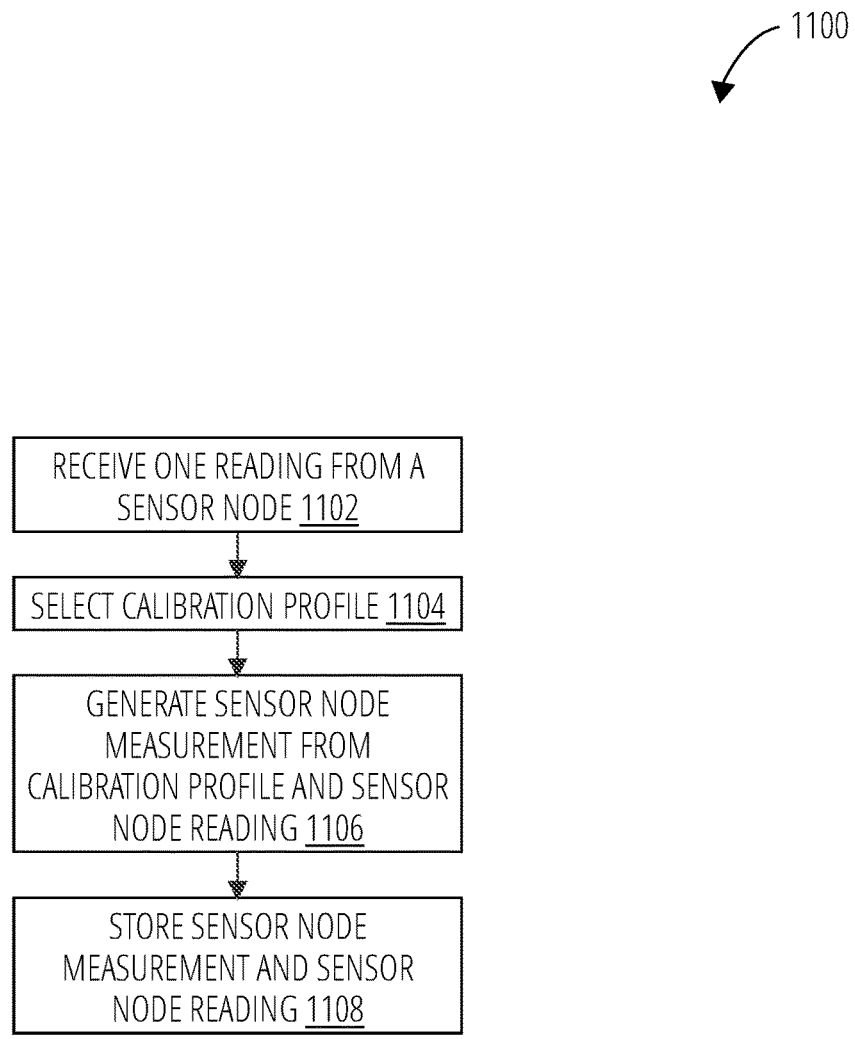
FIG. 11 illustrates an embodiment of a calibration method 1100.

FIG. 11 illustrates the method utilized by a data management platform to correct the measurements acquired by a sensor node by applying a calibration profile in accordance with certain embodiments of the disclosed subject matter.

A calibration method 1100 comprises the data management platform receiving one measurement from the sensor node (block 1102). The data management platform selects a calibration profile from the calibration profiles stored in storage media (block 1104). To select a calibration profile, the data management platform retrieves information about the node that acquired the measurement in block 1102, and information about the co-location pair that generated the calibration profile. In some embodiments the data management platform selects the calibration profile generated by the co-location pair whose reference monitor is closest to the sensor node that acquired the measurement. In other embodiments other selection criteria are used to select the calibration profile, where the selection criteria might make use of information including but not limited to land use information, meteorological information, and traffic information.

The data management platform may use the selected calibration profile to correct the sensor node measurement (block 1106). To correct the sensor node measurement, the data management platform uses the calibration constant within the calibration profile according to the calibration model within the calibration profile. Next, the data management platform may store the corrected sensor node measurement and the original sensor node measurement in storage media (block 1108).

In some embodiments, determining the calibration profile and applying the calibration profile for each of the first sensor node and the plurality of sensor nodes may be performed at a host in communication with the first sensor node, reference monitor, and plurality of sensor nodes by way of a network. This host may be a computing device such as the one illustrated in FIG. 13.

In some embodiments, applying the calibration profile for each of the first sensor node and the plurality of sensor nodes may further comprise communicating the calibration profile for each of the first sensor node and the plurality of sensor nodes to each of the first sensor node and the plurality of sensor nodes such that the first sensor node and the plurality of sensor nodes apply the calibration profile to generate calibrated measurement data. This communication may take place over a network as illustrated in FIG. 9.

Figure 12:
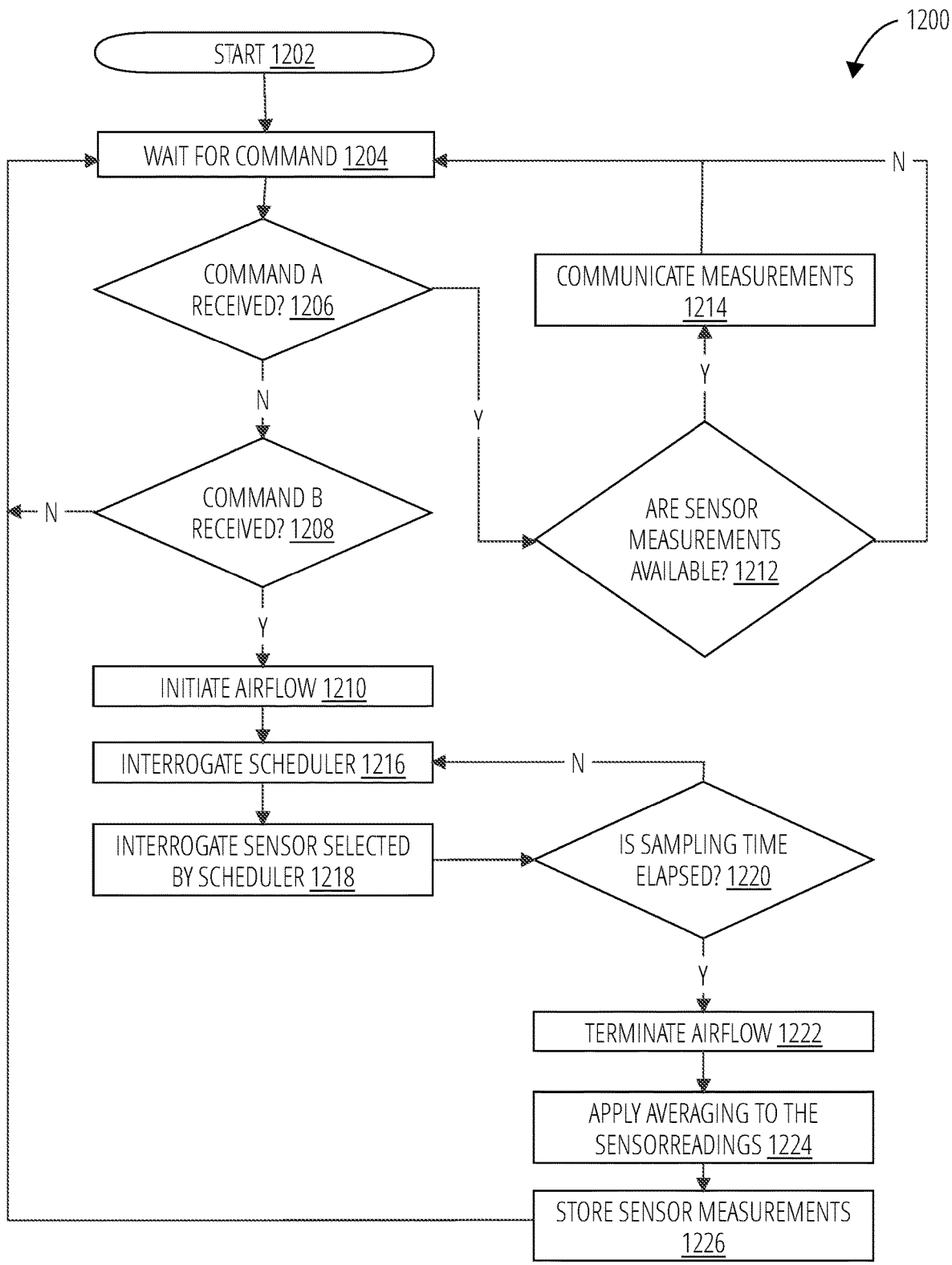
FIG. 12 illustrates an embodiment of a sensor module measurement method 1200.

FIG. 12 illustrates a sensor module measurement method 1200 in accordance with one embodiment. The sensor module measurement method 1200 comprises a start block 1202 and a state of waiting for a command (block 1204). If a command A is received (decision block 1206), then a determination is made as to whether sensor measurements are available (decision block 1212). In an embodiment, a command A is a request for sensor measurements. If the sensor measurements are available, then the measurements are communicated to the host device (such as the sensor node) via the sensor node controller 718 via serial interface (block 1214), and the method waits for an additional command (block 1204). The method also waits for an additional command if the sensor measurements are not available and communicates an error to the host device.

If a command A has not been received, then the method determines if a command B has been received (decision block 1208). In an embodiment, a command B is a request to initiate a sensor sampling procedure. If no command B has been received, then the method waits for an additional command (block 1204). Upon verification that a command B has been received, air flow is initiated in the sensor module (block 1210). Next, a scheduler is interrogated to initiate a timer and select a sensor in the sensor module (block 1216). The sensor selected by the scheduler is read and its reading is stored in a buffer (block 1218). The microcontroller checks if the sampling time has elapsed (decision block 1220). If the sampling time has not elapsed, then the scheduler is interrogated again (block 1216). If the sampling time has elapsed, then the air flow is terminated (block 1222). Next, the sensor measurements that are stored in the buffer are averaged (block 1224) and the final sensor measurements are stored (block 1226). In another embodiment, the sensor measurements that are stored in the buffer may be further processed with the aim of increasing measurement accuracy and reducing measurement noise. The method may then return to a state of waiting for a command (block 1204) and can return the final sensor measurements when requested by the host device. Command A and command B above are exemplary commands and are not limited thereto.

FIG. 13 is an example block diagram of a computing device 1300 that may incorporate embodiments of the solution. FIG. 13 is merely illustrative of a machine system to carry out aspects of the technical processes described herein and does not limit the scope of the claims. One of ordinary skill in the art would recognize other variations, modifications, and alternatives. In certain embodiments, the computing device 1300 includes a graphical user interface 1302, a data processing system 1304, a communication network 1306, communication network interface 1308, input device(s) 1310, output device(s) 1312, and the like.

As depicted in FIG. 13, the data processing system 1304 may include one or more processor(s) 1314 and a storage subsystem 1316. "Processor" refers to any circuitry, component, chip, die, package, or module configured to receive, interpret, decode, and execute machine instructions. Examples of a processor may include, but are not limited to, a central processing unit, a general-purpose processor, an application-specific processor, a graphics processing unit (GPU), a field programmable gate array (FPGA), Application Specific Integrated Circuit (ASIC), System on a Chip (SoC), virtual processor, processor core, and the like. The processor(s) 1314 communicate with a number of peripheral devices via a bus subsystem 1318. These peripheral devices may include input device(s) 1310, output device(s) 1312, communication network interface 1308, and the storage subsystem 1316. The storage subsystem 1316, in one embodiment, comprises one or more storage devices and/or one or more memory devices. In one embodiment, storage devices may be block storage devices. "Storage device" refers to any hardware, system, sub-system, circuit, component, module, non-volatile memory media, hard disk drive, storage array, device, or apparatus configured, programmed, designed, or engineered to store data for a period of time and retain the data in the storage device while the storage device is not using power from a power supply. Examples of storage devices include, but are not limited to, a hard disk drive, FLASH memory, MRAM memory, a solid-state storage device, Just a Bunch Of Disks (JBOD), Just a Bunch Of Flash (JBOF), an external hard disk, an internal hard disk, and the like. "Memory" refers to any hardware, circuit, component, module, logic, device, or apparatus configured, programmed, designed, arranged, or engineered to retain data. Certain types of memory require availability of a constant power source to store and retain the data. Other types of memory retain and/or store the data when a power source is unavailable. "Block storage device" refers to a storage device configured to interface with external hosts, servers, components, controllers and the like according to a block protocol. This means that under normal operating conditions data stored on the storage media of the block storage device is accessible by storage command that operate on one or more data blocks. Access to data of the block storage device is not available under normal operating conditions in quantities smaller than that defined for a data block. In other words, normal operations with a block storage device do not permit access to data at a word, byte, or bit level.

In one embodiment, the storage subsystem 1316 includes a volatile memory 1320 and a non-volatile memory 1322. The volatile memory 1320 and/or the non-volatile memory 1322 may store computer-executable instructions that alone or together form logic 1324 that when applied to, and executed by, the processor(s) 1314 implement embodiments of the processes disclosed herein. "Volatile memory" refers to a shorthand name for volatile memory media. In certain embodiments, volatile memory refers to the volatile memory media and the logic, controllers, processor(s), state machine(s), and/or other periphery circuits that manage the volatile memory media and provide access to the volatile memory media. "Volatile memory media" refers to any hardware, device, component, element, or circuit configured to maintain an alterable physical characteristic used to represent a binary value of zero or one for which the alterable physical characteristic reverts to a default state that no longer represents the binary value when a primary power source is removed or unless a primary power source is used to refresh the represented binary value. Examples of volatile memory media include but are not limited to dynamic random-access memory (DRAM), static random-access memory (SRAM), double data rate random-access memory (DDR RAM) or other random-access solid-state memory.

While the volatile memory media is referred to herein as "memory media," in various embodiments, the volatile memory media may more generally be referred to as volatile memory.

In certain embodiments, data stored in volatile memory media is addressable at a byte level which means that the data in the volatile memory media is organized into bytes (8 bits) of data that each have a unique address, such as a logical address. "Non-volatile memory" refers to a shorthand name for non-volatile memory media. In certain embodiments, non-volatile memory media refers to the non-volatile memory media and the logic, controllers, processor(s), state machine(s), and/or other periphery circuits that manage the non-volatile memory media and provide access to the non-volatile memory media.

"Non-volatile memory media" refers to any hardware, device, component, element, or circuit configured to maintain an alterable physical characteristic used to represent a binary value of zero or one after a primary power source is removed. Examples of the alterable physical characteristic include, but are not limited to, a threshold voltage for a transistor, an electrical resistance level of a memory cell, a current level through a memory cell, a magnetic pole orientation, a spin-transfer torque, and the like. The alterable physical characteristic is such that, once set, does not change so much when a primary power source for the non-volatile memory media is unavailable the alterable physical characteristic can be measured, detected, or sensed, when the binary value is read, retrieved, or sensed. Said another way, non-volatile memory media is a storage media configured such that data stored on the non-volatile memory media is retrievable after a power source for the non-volatile memory media is removed and then restored.

Examples of non-volatile memory media include but are not limited to: ReRAM, Memristor memory, programmable metallization cell memory, phase-change memory (PCM, PCME, PRAM, PCRAM, ovonic unified memory, chalcogenide RAM, or C-RAM), NAND flash memory (e.g., 2D NAND flash memory, 3D NAND flash memory), NOR flash memory, nano random access memory (nano RAM or NRAM), nanocrystal wire-based memory, silicon-oxide based sub-10 nanometer process memory, graphene memory, Silicon-Oxide-Nitride-Oxide-Silicon (SONOS), programmable metallization cell (PMC), conductive-bridging RAM (CBRAM), magneto-resistive RAM (MRAM), magnetic storage media (e.g., hard disk, tape), optical storage media, or the like. While the non-volatile memory media is referred to herein as "memory media," in various embodiments, the non-volatile memory media may more generally be referred to as non-volatile memory. Because non-volatile memory media is capable of storing data when a power supply is removed, the non-volatile memory media may also be referred to as a recording media, non-volatile recording media, storage media, storage, non-volatile memory, volatile memory medium, non-volatile storage medium, non-volatile storage, or the like.

In certain embodiments, data stored in non-volatile memory media is addressable at a block level which means that the data in the non-volatile memory media is organized into data blocks that each have a unique logical address (e.g., LBA). In other embodiments, data stored in non-volatile memory media is addressable at a byte level which means that the data in the non-volatile memory media is organized into bytes (8 bits) of data that each have a unique address, such as a logical address. One example of byte addressable non-volatile memory media is storage class memory (SCM). "Logic" refers to machine memory circuits, non-transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter). "Partition identifier" refers to any identifier for a logical partition or physical partition.

The input device(s) 1310 include devices and mechanisms for inputting information to the data processing system 1304. These may include a keyboard, a keypad, a touch screen incorporated into the graphical user interface 1302, audio input devices such as voice recognition systems, microphones, and other types of input devices. In various embodiments, the input device(s) 1310 may be embodied as a computer mouse, a trackball, a track pad, a joystick, wireless remote, drawing tablet, voice command system, eye tracking system, and the like. The input device(s) 1310 typically allow a user to select objects, icons, control areas, text and the like that appear on a graphical user interface 1302 via a command such as a click of a button or the like.

The output device(s) 1312 include devices and mechanisms for outputting information from the data processing system 1304. These may include the graphical user interface 1302, speakers, printers, infrared LEDs, and so on, as well understood in the art. In certain embodiments, the graphical user interface 1302 is coupled to the bus subsystem 1318 directly by way of a wired connection. In other embodiments, the graphical user interface 1302 couples to the data processing system 1304 by way of the communication network interface 1308. For example, the graphical user interface 1302 may comprise a command line interface on a separate computing device 1300 such as desktop, server, or mobile device.

The communication network interface 1308 provides an interface to communication networks (e.g., communication network 1306) and devices external to the data processing system 1304. The communication network interface 1308 may serve as an interface for receiving data from and transmitting data to other systems. Embodiments of the communication network interface 1308 may include an Ethernet interface, a modem (telephone, satellite, cable, ISDN), (asynchronous) digital subscriber line (DSL), FireWire, USB, a wireless communication interface such as Bluetooth or WiFi, a near field communication wireless interface, a cellular interface, and the like.

The communication network interface 1308 may be coupled to the communication network 1306 via an antenna, a cable, or the like. In some embodiments, the communication network interface 1308 may be physically integrated on a circuit board of the data processing system 1304, or in some cases may be implemented in software or firmware, such as "soft modems", or the like.

The computing device 1300 may include logic that enables communications over a network using protocols such as HTTP, TCP/IP, RTP/RTSP, IPX, UDP and the like.

The volatile memory 1320 and the non-volatile memory 1322 are examples of tangible storage media configured to store computer readable data and instructions to implement various embodiments of the processes described herein. "Storage media" refers to any physical media organized and configured to store one or more bits of data. In one embodiment, storage media refers to physical storage cells and/or memory cells used in volatile memory media. In another embodiment, storage media refers to physical storage cells and/or memory cells used in non-volatile memory media. Other types of tangible media include removable memory (e.g., pluggable USB memory devices, mobile device SIM cards), optical storage media such as CD-ROMS, DVDs, semiconductor memories such as flash memories, non-transitory read-only-memories (ROMS), battery-backed volatile memories, networked storage devices, and the like. The volatile memory 1320 and the non-volatile memory 1322 may be configured to store the basic programming and data constructs that provide the functionality of the disclosed processes and other embodiments thereof that fall within the scope of the present invention.

Logic 1324 that implements one or more parts of embodiments of the solution may be stored in the volatile memory 1320 and/or the non-volatile memory 1322. Logic 1324 may be read from the volatile memory 1320 and/or non-volatile memory 1322 and executed by the processor(s) 1314. The volatile memory 1320 and the non-volatile memory 1322 may also provide a repository for storing data used by the logic 1324.

The volatile memory 1320 and the non-volatile memory 1322 may include a number of memories including a main random-access memory (RAM) for storage of instructions and data during program execution and a read only memory (ROM) in which read-only non-transitory instructions are stored. The volatile memory 1320 and the non-volatile memory 1322 may include a file storage subsystem providing persistent (non-volatile) storage for program and data files. The volatile memory 1320 and the non-volatile memory 1322 may include removable storage systems, such as removable flash memory.

The bus subsystem 1318 provides a mechanism for enabling the various components and subsystems of data processing system 1304 communicate with each other as intended. Although the communication network interface 1308 is depicted schematically as a single bus, some embodiments of the bus subsystem 1318 may utilize multiple distinct busses.

It will be readily apparent to one of ordinary skill in the art that the computing device 1300 may be a device such as a smartphone, a desktop computer, a laptop computer, a rack-mounted computer system, a computer server, or a tablet computer device. As commonly known in the art, the computing device 1300 may be implemented as a collection of multiple networked computing devices. Further, the computing device 1300 will typically include operating system logic (not illustrated) the types and nature of which are well known in the art.

Terms used herein should be accorded their ordinary meaning in the relevant arts, or the meaning indicated by their use in context, but if an express definition is provided, that meaning controls.

"Circuitry" refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment). "Firmware" refers to software logic embodied as processor-executable instructions stored on volatile memory media and/or non-volatile memory media. "Hardware", in certain embodiments, refers to logic embodied as analog and/or digital circuitry. "Software" refers to logic implemented as processor-executable instructions in a machine memory (e.g. read/write volatile memory media or non-volatile memory media).

Various functional operations described herein may be implemented in logic that is referred to using a noun or noun phrase reflecting said operation or function. For example, an association operation may be carried out by an "associator" or "correlator". Likewise, switching may be carried out by a "switch", selection by a "selector", and so on.

Within this disclosure, different entities (which may variously be referred to as "units," "circuits," other components, etc.) may be described or claimed as "configured" to perform one or more tasks or operations. This formulation—[entity] configured to [perform one or more tasks]—is used herein to refer to structure (i.e., something physical, such as an electronic circuit). More specifically, this formulation is used to indicate that this structure is arranged to perform the one or more tasks during operation. A structure can be said to be "configured to" perform some task even if the structure is not currently being operated. A "credit distribution circuit configured to distribute credits to a plurality of processor cores" is intended to cover, for example, an integrated circuit that has circuitry that performs this function during operation, even if the integrated circuit in question is not currently being used (e.g., a power supply is not connected to it). Thus, an entity described or recited as "configured to" perform some task refers to something physical, such as a device, circuit, memory storing program instructions executable to implement the task, etc. This phrase is not used herein to refer to something intangible.

The term "configured to" is not intended to mean "configurable to." An unprogrammed FPGA, for example, would not be considered to be "configured to" perform some specific function, although it may be "configurable to" perform that function after programming.

Reciting in the appended claims that a structure is "configured to" perform one or more tasks is expressly intended not to invoke 35 U.S.C. § 112(f) for that claim element. Accordingly, claims in this application that do not otherwise include the "means for" [performing a function] construct should not be interpreted under 35 U.S.C. § 112(f).

As used herein, the term "based on" is used to describe one or more factors that affect a determination. This term does not foreclose the possibility that additional factors may affect the determination. That is, a determination may be solely based on specified factors or based on the specified factors as well as other, unspecified factors. Consider the phrase "determine A based on B." This phrase specifies that B is a factor that is used to determine A or that affects the determination of A. This phrase does not foreclose that the determination of A may also be based on some other factor, such as C. This phrase is also intended to cover an embodiment in which A is determined based solely on B. As used herein, the phrase "based on" is synonymous with the phrase "based at least in part on."

As used herein, the phrase "in response to" describes one or more factors that trigger an effect. This phrase does not foreclose the possibility that additional factors may affect or otherwise trigger the effect. That is, an effect may be solely in response to those factors, or may be in response to the specified factors as well as other, unspecified factors. Consider the phrase "perform A in response to B." This phrase specifies that B is a factor that triggers the performance of A. This phrase does not foreclose that performing A may also be in response to some other factor, such as C. This phrase is also intended to cover an embodiment in which A is performed solely in response to B.

As used herein, the terms "first," "second," etc. are used as labels for nouns that they precede, and do not imply any type of ordering (e.g., spatial, temporal, logical, etc.), unless stated otherwise. For example, in a register file having eight registers, the terms "first register" and "second register" can be used to refer to any two of the eight registers, and not, for example, just logical registers 0 and 1.

When used in the claims, the term "or" is used as an inclusive or and not as an exclusive or. For example, the phrase "at least one of x, y, or z" means any one of x, y, and z, as well as any combination thereof.

"Data management platform" in this context refers to a centralized system for collecting and analyzing large sets of data originating from disparate sources. A data management platform creates a combined development and delivery environment that provides users with consistent, accurate and timely data. At its simplest, a data management platform could be a database management system that imports data from many systems and enables users to view the data in a consistent manner. A high-end data management platform might combine data management technologies and data analytics tools into a single software suite. A key role of a data management platform is to collect structured and unstructured data from a range of internal and external sources, and to then integrate and store that data. These platforms also analyze and organize data to provide insight to data-driven parts of the business.

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods and media for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow. Having thus described illustrative embodiments in detail, it will be apparent that modifications and variations are possible without departing from the scope of the invention as claimed. The scope of inventive subject matter is not limited to the depicted embodiments but is rather set forth in the following Claims.

What is claimed is:

1. A method for generating information about a system, wherein the system comprises a data management platform, a first reference gas monitor positioned at a first reference gas monitor location, a first gas sensor node, and a second gas sensor node, the method comprising:
    positioning the first gas sensor node at a first gas sensor node location that is within a distance limit of the first reference gas monitor location;
    positioning the second gas sensor node at a second gas sensor node location, wherein the second gas sensor node location is further away from the first reference gas monitor location than the first gas sensor node location is from the first reference gas monitor location;
    periodically gathering over a time interval, using the first reference gas monitor, gas quality measurement data for the first reference gas monitor location;
    periodically gathering over the time interval, using the first gas sensor node positioned at the first gas sensor node location, gas quality measurement data for the first gas sensor node location;
    calculating, using the data management platform, a calibration profile for the first gas sensor node based on:
        the gathered gas quality measurement data for the first reference gas monitor location; and
        the gathered gas quality measurement data for the positioned first gas sensor node location;
    applying the calculated calibration profile to gas quality measurement data gathered by the second gas sensor node positioned at the second gas sensor node location to obtain calibrated gas quality measurement data for the second gas sensor node location; and
    storing the calibrated gas quality measurement data for the second gas sensor node location in storage media of the system.

2. The method of claim 1, wherein the first reference gas monitor comprises an air quality monitoring station operated by a governmental agency and with measurement accuracy higher than the accuracy of the first gas sensor node.

3. The method of claim 1, wherein the calculating comprises determining a plurality of calibration constants of the calibration profile by fitting a calibration model of the calibration profile to the gathered gas quality measurement data for the first reference gas monitor location and to the gathered gas quality measurement data for the first gas sensor node location.

4. The method of claim 3, wherein the applying comprises multiplying the gathered gas quality measurement data for the second gas sensor node location with a calibration constant of the plurality of calibration constants of the calculated calibration profile.

5. The method of claim 4, wherein the applying further comprises multiplying another calibration constant of the plurality of calibration constants with one of a temperature measurement of the system or a humidity measurement of the system.

6. The method of claim 3, wherein a calibration constant of the plurality of calibration constants comprises an offset coefficient.

7. The method of claim 3, wherein a calibration constant of the plurality of calibration constants comprises a bias coefficient.

8. The method of claim 3, wherein:
    a first calibration constant of the plurality of calibration constants comprises an offset coefficient; and
    a second calibration constant of the plurality of calibration constants comprises a bias coefficient.

9. The method of claim 3, wherein the calibration model is a linear model.

10. The method of claim 3, further comprising, after the calculating, applying the calculated calibration profile to gas quality measurement data gathered by the first gas sensor node to obtain calibrated gas quality measurement data for the first gas sensor node location.

11. The method of claim 10, wherein the applying comprises multiplying the gathered gas quality measurement data for the first gas sensor node location with a calibration constant of the plurality of calibration constants of the calculated calibration profile.

12. The method of claim 11, wherein the applying further comprises multiplying another calibration constant of the plurality of calibration constants with one of a temperature measurement of the system or a humidity measurement of the system.

13. The method of claim 1, wherein the first reference gas monitor is operated by a governmental agency.

14. The method of claim 1, wherein the measurement accuracy of data gathering by the first reference gas monitor is higher than the measurement accuracy of data gathering by the first gas sensor node.

15. The method of claim 1, wherein the magnitude of the distance limit is defined such that, if the distance between a gas sensor node and a reference gas monitor is lower than the magnitude of the distance limit, then the reference gas monitor and the gas sensor node are accurately considered to be exposed to the same concentration of air pollutants.

16. The method of claim 1, further comprising wirelessly communicating the calculated calibration profile to the first gas sensor node.

17. The method of claim 16, further comprising, prior to the calculating, wirelessly communicating the gathered gas quality measurement data for the first gas sensor node location to the data management platform.

18. The method of claim 1, further comprising, prior to the calculating, wirelessly communicating the gathered gas quality measurement data for the first gas sensor node location to the data management platform.

19. The method of claim 1, wherein the second gas sensor node location is not within the distance limit of the first reference gas monitor location.

20. The method of claim 19, wherein the magnitude of the distance limit is defined such that, if the distance between a gas sensor node and a reference gas monitor is lower than the magnitude of the distance limit, then the reference gas monitor and the gas sensor node are accurately considered to be exposed to the same concentration of air pollutants.

21. A method for generating information about a system, wherein the system comprises a data management platform, a first reference monitor positioned at a first reference monitor location, and a first sensor node positioned at a first sensor node location that is within a distance limit of the first reference monitor location, wherein the system further comprises a second reference monitor positioned at a second reference monitor location, a second sensor node positioned at a second sensor node location that is within the distance limit of the second reference monitor location, and a third sensor node positioned at a third sensor node location that is outside the distance limit of the first reference monitor location and that is outside the distance limit of the second reference monitor location, the method comprising:
  periodically gathering over a time interval, using the first reference monitor, gas measurement data for the first reference monitor location;
  periodically gathering over the time interval, using the first sensor node, gas measurement data for the first sensor node location;
  calculating, using the data management platform, a first calibration profile for the first sensor node based on:
    the gathered gas measurement data for the first reference monitor location; and
    the gathered gas measurement data for the first sensor node location;
  selecting, using the data management platform, a particular calibration profile for the third sensor node from a plurality of calibration profiles that comprises the first calibration profile for the first sensor node and a second calibration profile for the second sensor node;
  gathering, using the third sensor node, gas measurement data for the third sensor node location;
  applying the selected particular calibration profile to the gathered gas measurement data for the third sensor node location to obtain calibrated measurement data for the third sensor node location; and
  storing the calibrated measurement data for the third sensor node location in storage media.

22. The method of claim 21, wherein the gathering the gas measurement data for the third sensor node location occurs prior to the selecting.

23. The method of claim 22, further comprising receiving the gathered gas measurement data for the third sensor node location at the data management platform from the third sensor node, wherein the applying comprises applying, using the data management platform, the selected particular calibration profile to the received gathered gas measurement data for the third sensor node location to obtain the calibrated measurement data for the third sensor node location.

24. The method of claim 21, further comprising receiving the gathered gas measurement data for the third sensor node location at the data management platform from the third sensor node, wherein the applying comprises applying, using the data management platform, the selected particular calibration profile to the received gathered gas measurement data for the third sensor node location to obtain the calibrated measurement data for the third sensor node location.

25. The method of claim 21, wherein the selecting occurs prior to the gathering the gas measurement data for the third sensor node location.

26. The method of claim 25, further comprising receiving the selected particular calibration profile at the third sensor node from the data management platform, wherein the applying comprises applying, using the third sensor node, the received selected particular calibration profile to the gathered gas measurement data for the third sensor node location to obtain the calibrated measurement data for the third sensor node location.

27. The method of claim 21, further comprising receiving the selected particular calibration profile at the third sensor node from the data management platform, wherein the applying comprises applying, using the third sensor node, the received selected particular calibration profile to the gathered gas measurement data for the third sensor node location to obtain the calibrated measurement data for the third sensor node location.

28. The method of claim 21, wherein:
  the selecting comprises selecting the first calibration profile as the particular calibration profile for the third sensor node when the third sensor node location is closer to the first reference monitor location than to the second reference monitor location; and
  the selecting comprises selecting the second calibration profile as the particular calibration profile for the third sensor node when the third sensor node location is closer to the second reference monitor location than to the first reference monitor location.

29. The method of claim 21, wherein the selecting comprises selecting the particular calibration profile for the third sensor node based on at least one of:
  land use information;
  meteorological information; or
  traffic information.

30. A method for generating information about a system, wherein the system comprises a data management platform, a first reference gas monitor positioned at a first reference monitor location, and a first gas sensor node positioned at a first sensor node location that is within a distance limit of the first reference monitor location, wherein the system further comprises a second reference gas monitor positioned at a second reference monitor location, a second gas sensor node positioned at a second sensor node location that is within the distance limit of the second reference monitor location, and a third gas sensor node positioned at a third sensor node location that is not within the distance limit of the first reference monitor location and that is not within the distance limit of the second reference monitor location, the method comprising:
  gathering over a first time interval, using the first reference gas monitor, gas quality measurement data for the first reference monitor location;

gathering over the first time interval, using the first gas sensor node, gas quality measurement data for the first sensor node location;
calculating a first calibration profile for the first gas sensor node based on the gathered gas quality measurement data for the first reference monitor location;
storing the first calibration file in the system;
gathering over a second time interval, using the second reference gas monitor, gas quality measurement data for the second reference monitor location;
gathering over the second time interval, using the second gas sensor node, gas quality measurement data for the second sensor node location;
calculating a second calibration profile for the second gas sensor node based on the gathered gas quality measurement data for the second reference monitor location;
storing the second calibration file in the system;
selecting a particular calibration profile for the third gas sensor node from the stored first calibration profile for the first gas sensor node and the stored second calibration profile for the second gas sensor node; and
applying the selected particular calibration profile to gas quality measurement data for the third sensor node location to obtain calibrated measurement data for the third sensor node location.

* * * * *